(12) United States Patent
Wagner et al.

(10) Patent No.: US 8,785,186 B2
(45) Date of Patent: Jul. 22, 2014

(54) HYBRID CELLS FOR TREATING CANCER PATIENTS

(75) Inventors: Thomas E. Wagner, Greer, SC (US); Yanzhang Wei, Greer, SC (US)

(73) Assignee: Orbis Health Solutions LLC, Greenville, SC (US)

(*) Notice: Subject to any disclaimer, the term of this patent is extended or adjusted under 35 U.S.C. 154(b) by 101 days.

(21) Appl. No.: 12/461,760

(22) Filed: Aug. 24, 2009

(65) Prior Publication Data

US 2010/0047288 A1 Feb. 25, 2010

Related U.S. Application Data

(60) Continuation of application No. 11/802,566, filed on May 23, 2007, now abandoned, which is a continuation-in-part of application No. 11/017,733, filed on Dec. 22, 2004, now abandoned, which is a division of application No. 09/756,293, filed on Jan. 9, 2001, now Pat. No. 6,849,451.

(60) Provisional application No. 60/175,376, filed on Jan. 11, 2000, provisional application No. 60/924,611, filed on May 22, 2007.

(51) Int. Cl.
*C12N 5/00* (2006.01)
*A01N 63/00* (2006.01)

(52) U.S. Cl.
USPC .......... 435/346; 435/325; 424/93.1; 424/93.7

(58) Field of Classification Search
None
See application file for complete search history.

(56) References Cited

U.S. PATENT DOCUMENTS

| | | | |
|---|---|---|---|
| 4,762,701 | A | 8/1988 | Horan et al. |
| 4,783,401 | A | 11/1988 | Horan et al. |
| 4,859,584 | A | 8/1989 | Horan et al. |
| 5,316,911 | A * | 5/1994 | Baek et al. ............ 435/7.9 |
| 6,652,848 | B1 | 11/2003 | Gong et al. |
| 7,297,330 | B2 | 11/2007 | Berd |
| 2001/0012632 | A1 | 8/2001 | Moser et al. |
| 2002/0141973 | A1 | 10/2002 | Moser et al. |
| 2003/0031656 | A1 | 2/2003 | Moser et al. |
| 2003/0118562 | A1 | 6/2003 | Moser et al. |

FOREIGN PATENT DOCUMENTS

| | | |
|---|---|---|
| WO | WO 90/03576 A1 | 4/1990 |
| WO | WO 96/30030 A1 | 10/1996 |
| WO | WO 98/46785 A1 | 10/1998 |

OTHER PUBLICATIONS

Holmes et al., "A Rapid, Novel Strategy to Induce Tumor Cell-Specific Cytotoxic T Lymphocyte Responses Using Instant Dendritomas," *Journal of Immunotherapy*, 2001, pp. 122-129, vol. 24, No. 2.

Schaap et al., "Gene expression in flow sorted mouse teratocarcinoma x human fibroblast heterokaryons," *Differentiation*, 1984, pp. 127-133, vol. 26, Springer-Verlag.

Stryer, *Biochemie*, Spektrum der Wissenschaften GmbH, 1990, pp. 931-933.

Parkinson et al., "Cytokines: Biology and Applications in Cancer Medicine", in Cancer Medicine, 4th ed., pp. 1213-1226.

Boon et al., "Tumor Antigens Recognized by T Cells", Elsevier Science Ltd., vol. 18:267-268, (1997).

Philip et al., "Treatment of Malignant Melanoma With Interleukin-2", *Seminars in Oncology*, vol. 24(1):S4-32, S4-38, (1997).

Smith et al., "Immune and Gene Therapy for Melanoma, and the Immunobiology of Melanoma", *International Journal of Dermatology*, Blackwell Science Ltd., vol. 38:490-508, (1999).

Stockert et al., "A Survey of the Humoral Immune Response of Cancer Patients to a Panel of Human Tumor Antigens", *J. Exp. Med.*, The Rockefeller University Press, vol. 187(8):1349-1354, (1998).

Sahin et al., "Human Neoplasms Elicit Multiple Specific Immune Responses in The Autologous Host", *Proc. Natl. Acad. Sci. USA*, Immunology, vol. 92:11810-11813, (1995).

Gabrilovich et al., "Production of Vascular Endothelial Growth Factor by Human Tumors Inhibits The Functional Maturation of Dendritic Cells", *Nature Medicine*, vol. 2(10):1096-1103, (1996).

Ishida et al., "Defective Function of Langerhans Cells in Tumor-Bearing Animals is the Result of Defective Maturation From Hemopoietic Progenitors", *The Journal of Immunology*, The American Association of Immunologists, pp. 4842-4851, (1998).

Steinman, "The Dendritic Cell System and Its Role in Immunogenicity", *Annu. Rev. Immunol.*, Annual Reviews Inc., vol. 9:271-296, (1991).

Macatonia et al., "Primary Stimulation by Dendritic Cells Induces Antiviral proliferative and Cytotoxic T Cell Responses in Vitro", *J. Exp. Med.*, The Rockefeller University Press, vol. 169:1255-1264, (1989).

Mehta-Damani et al., "Generation of Antigen-Specific CD8+ CTLs From Naïve Precursors", *The Journal of Immunology*, The American Association of Immunologists, vol. 153:996-1004, (1994).

Porgador et al., "Bone Marrow-Generated Dendritic Cells Pulsed With a Class I-Restricted peptide Are Potent Inducers of Cytotoxic T Lymphocytes", *J. Exp. Med.*, The Rockefeller University Press, vol. 182:255-260, (1995).

Young et al., "Dendritic Cells As Adjuvants for Class I Major Histocompatibility Complex-Restricted Antitumor Immunity", *J. Exp. Med.*, The Rockefeller University Press, vol. 183:7-12, (1996).

Mayordomo et al., "Bone Marrow-Derived Dendritic Cells Pulsed With Synthetic Tumour Peptides Elicit Protective and Therapeutic Antitumour Immunity", *Nature Medicine*, vol. 1(12):1297-1303, (1995).

Bakker et al., "Generation of Antimelanoma Cytotoxic T Lymphocytes From health Donors After Presentation of melanoma-Associated Antigen-Derived Epitopes by Dendritic Cells in Vitro", *Cancer Research*, vol. 55:5330-5334, (1995).

(Continued)

*Primary Examiner* — Janice Li
(74) *Attorney, Agent, or Firm* — Foley & Lardner LLP

(57) ABSTRACT

The present invention relates to cancer treatment compositions and methods for treating a specific cancer patient population. In particular, the application describes methods of treating a patient with cancer, such as a neuroblastoma, with a hybrid cell preparation.

17 Claims, 11 Drawing Sheets

(56) References Cited

OTHER PUBLICATIONS

Flamand et al., "Murine Dendritic Cells pulsed in Vitro With Tumor Antigen Induce Tumor Resistance in Vitro", *Eur. J. Immunol.* VCH Verlagsgesellschaft mbH, vol. 24:605-610, (1994).
Gong et al., "Induction of Antigen-Specific Antitumor Immunity With Adenovirus-Transduced Dendritic Cells", *Gene Therapy*, Stockton Press, vol. 4:1023-1028, (1997).
Song et al., "Dendritic Cells Genetically Modified With an Adenovirus Vector Encoding the cDNA for a Model Antigen Induce Protective and Therapeutic Antitumor Immunity", *J. Exp. Med.*, The Rockefeller University Press, vol. 186(8):1247-1256, (1997).
Specht et al., "Dendritic Cells Retrovirally Transduced With a Model Antigen Gene Are Therapeutically Effective Against Established Pulmonary Metastases", *The Journal of Experimental Medicine*, vol. 186(8):1213-1221, (1997).
Rosenberg et al., "Immunologic and Therapeutic Evaluation of a Synthetic Peptide Vaccine for the Treatment of Patients With Metastatic Melanoma", *Nature Medicine*, vol. 4(3):321-327, (1998).
Wallack et al., "A Phase III Randomized, Double-Blind, Multiinstitutional Trial of Vaccinia Melanoma Oncolysate-Active Specific Immunotherapy for Patients With Stage II Melanoma", *Cancer*, vol. 75(1):34-42 (1995).
Bystryn, "Clinical Activity of a Polyvalent Melanoma Antigen Vaccine", Springer-Verlag Berlin, vol. 139:337-348, (1995).
Mitchell, "Perspective on Allogeneic Melanoma Lysates in Active Specific Immunotherapy", *Seminars in Oncology*, vol. 25(6):623-635, (1998).
Morton et al., "Polyvalent Melanoma Vaccine Improves Survival of Patients With Metastatic Melanoma", *Ann. N. Y. Acad. Sci.*, vol. 690:120-134 (1993).
Berd et al., "Autologous, Hapten-Modified Vaccine as a Treatment for Human Cancers", *Seminars in Oncology*, vol. 25(6):646-653, (1998).
Berd et al., "Autologous Hapten-Modified Melanoma Vaccine As Postsurgical Adjuvant Treatment After Resection of Nodal Metastases", *Journal of Clinical Oncology*, vol. 15(6):2359-2370, (1997).
Shurin, "Dendritic Cells Presenting Tumor Antigen", *Cancer Immunol. Immunother*, vol. 43:158-164, (1996).
Gong et al., "Induction of Antitumor Activity by Immunization With Fusions of Dendritic and Carcinoma Cells", *Nature Medicine*, vol. 3(5):558-561, (1997).
Haigh et al., "Vaccine Therapy for patients With Melanoma", *Oncology*, vol. 13(11):1561-1574, (1999).
Wang et al., "Eliciting T Cell Immunity Against Poorly Immunogenic Tumors by Immunization With Dendritic Cell-Tumor Fusion Vaccines", *The Journal of Immunology*, The American Association of Immunologists, vol. 161:5516-5524, (1998).
Lespagnard et al., "Dendritic Cells Fused With Mastocytoma Cells Elicit Therapeutic Antitumor Immunity", *Int. J. Cancer*, vol. 76:250-258, (1998).
Rowse et al., "Tolerance and Immunity to MUC1 in a Human MUC1 Transgenic Murine Model", *Cancer Research*, vol. 58:315-321, (1998).
Abbas et al., "Cellular and Molecular Immunology", Saunders Text and Review Series, pp. 347-350 (1999).
Horan et al., "Stable Cell Membrane Labelling", *Nature*, vol. 340:167-168, (1989).
Wei et al., "Long-Term Expression of Human Growth Hormone (hGH) in Mice Containing Allogeneic Yolk Sac Cell Derived Neovascular Implants Expressing hGH", *Stem Cells*, vol. 14:2320238, (1996).

Horan et al., "Fluorescent Cell Labeling for In Vivo and In Vitro Cell Tracking", *Methods in Cell Biology*, Academic Press, Inc., vol. 33:469-491, (1990).
Michelson et al., "In Vivo Tracking of Platelets: Circulating Degranulated Platelets Rapidly Lose Surface P-Selectin But Continue to Circulate and Function", *Proc. Natl., Acad. Sci. USA*, vol. 93:11877-11882, (1996).
Zitvogel et al., "Therapy of Murine Tumors With Tumor Peptide-Pulsed Dendritic Cells: Dependence on T Cells, B7 Costimulation, and T Helper Cell 1-Associated Cytokines", *J. Exp. Med.*, The Rockefeller University Press, vol. 183:87-97, (1996).
Gimmi et al., "Breast Cancer-Associated Antigen, DF3/MUC1, Induces Apoptosis of Activated Human T Cells", *Nature Medicine*, vol. 2(12):1367-1370, (1996).
Yeh et al., "Expression of B7-1 by Pam 212 Squamous Cell Carcinoma Enhances Tumor Cell Infractions With, Dendritic Epidermal T Cells But Does Not Affect in Vivo Tumor Growth", *J. Invest. Dermatol.*, vol. 109:728-733, (1997).
Koolwijk et al., Enrichment and Selection of Hybrid Hybridomas by Percoll Density Gradient Centrifugation and Foluorescent-Activated Cell Sorting, No. 2, pp. 217-225 (1988).
Ohkohchi et al., "New Technique for Producing Hybridoma by Using Laser Radiation," (2002).
Wagner et al., A Somatic Cell Hybrid Panel for Distal 17q: GDIA1 maps to 17q25.3, pp. 172-175 (1997).
Kim et al, J. Immunol. No. 162, pp. 6855-6866 (1999).
Zhou et al., J. Immunol., No. 167, pp. 7126-7133 (2001).
Kalden et al., Advances in Immunol., No. 68, pp. 333-395 (1998).
Thompson et al., Immunol. Cell Bio., No. 80, pp. 509-519 (2002).
Subculture, Wikipedia, 2008.
Primary Culture, Answer.com 2008.
Dillman, Cancer Biother. Radiopharm., No. 14, pp. 443-449 (1999).
Celluzzi et al., Cutting edge: Physical Interaction between Dendritic Cells and Tumor Cells Results in an Immunogen that Induces Protective and Therapeutic Tumor Rejection. The Journ. of Immunol., vol. 160, pp. 3081-3085 (1998).
Trefzer et al., A phase I Trial with a Hybrid Cell Vaccine in Patents with Metastatic Melanoma. Gene Therapy of Cancer (1998).
Li et al., "Purified Hybrid Cells from Dendritic Cell and Tumor Cell Fusions are Superior Activators of Antitumor Immunity," Cancer Immunol. Immunother, vol. 50, pp. 456-462 (2001).
Haenssle, Curr. Opinion. Invest. Drugs, vol. 6, pp. 1240-1245 (2005).
Bodey et al., Anticancer Res., vol. 20, pp. 2665-2676 (2000).
Cebon et al., Austral. J. Dermatol., vol. 58, pp. S66-S72 (1997).
Powell et al., J. Immunol., vol. 177, pp. 6527-6539 (2006).
Yu et al., J. Clin. Invest., vol. 289, pp. 110-194 (2002).
McWilliams et al., J. Immunol., vol. 177, pp. 155-161 (2006).
Office Action in related U.S. Appl. No. 11/802,566, 8 pgs, dated Sep. 28, 2009.
Necheles et al., "Immunochemotherapy in Advanced Neuroblastoma," *Cancer*, No. 41, vol. 4, pp. 1282-1288 (1978).
Official Communication cited by the EPO in a related EP application No. 05005671.2, dated Nov. 8, 2010, 7 pages.
Karawajew, B. Micheel, et al., "Bispecific Antibody-Producing Hybrid Hybridomas Selected by a Fluorescence Activated Cell Sorter", *Journal of Immunological Methods*, (1987), 96, pp. 265-270.
Garrovillo et al., "Indirect Allorecognition in Acquired Thymic Tolerance: Induction of Donor-Specific Tolerance to Rat Cardiac Allografts by Allopeptide-Pulsed Host Dendritic Cells," Transplantation, Dec. 27, 1999, 68(12):1827-1834.
Van Elsas et al., "Transfection of IL-2 Augments CTL Response to Human Melanoma Cells in Vitro: Immunological Characterization of a Melanoma Vaccine," Journal of Immunotherapy, 1997, 20(5):343-350.

\* cited by examiner

Human Dendritic Cells

HYBRID CELLS FOR TREATING CANCER PATIENTS

CROSS-REFERENCE TO RELATED APPLICATIONS

This application is a continuation of U.S. patent application Ser. No. 11/802,566, filed May 23, 2007 now abandoned, which claims priority to U.S. Provisional Patent Application 60/924,611, filed May 22, 2007; and which is also a continuation-in-part of U.S. patent application Ser. No. 11/017,733, filed Dec. 22, 2004, now abandoned which is a Divisional of U.S. patent application Ser. No. 09/756,293, filed Jan. 9, 2001, now U.S. Pat. No. 6,849,451, which claims priority from U.S. Provisional Patent Application Ser. No. 60/175,376, filed Jan. 11, 2000. The entirety of these applications are incorporated herein by reference.

BACKGROUND OF THE INVENTION

The present invention relates to hybrid cells and methods of making and using hybrid cells. Perhaps the most substantial practical application of hybrid cells is the production of hybridomas, which are used to produce monoclonal antibodies. In addition, they are used in a variety instances for research purposes, but their broader application, for example, in a clinical treatment setting has heretofore not been practical. These clinical applications include the cellular vaccines for treating or preventing cancer and other disorders, as well as preventing transplant rejection. The present invention responds to such deficiencies by providing methods and reagents that make the broad applicability of hybrid cells a reality.

Recent advances in molecular immunology now make immunotherapy a truly viable option for the treatment of patients with cancer and metastatic disease. The past decade has seen the approval and introduction of several immunotherapeutic strategies for wide ranging use against several metastatic cancers, Parkinson et al., in CANCER MEDICINE, 4$^{th}$ ed., pp. 1213-1226 (Holland et al., eds. 1997). Perhaps the best known strategies include IL-2 therapy (Philip et al., *Seminars in Oncology.* 24(1 Suppl 4): S32-8, 1997 February) and tumor vaccines targeted against melanoma. Smith et al., *Int J Dermatol* 1999; 38(7): 490-508. While these strategies are efficacious against some tumors, their potency is limited because they only enhance the already enfeebled ability of tumor cells to present their "foreign" epitopes to CD8+ T-cells, and to generate thereby a tumor-specific cytotoxic T lymphocyte (CTL) response.

Autologous whole tumor cell-based vaccines were first used for immunotherapy of malignant melanoma. Such whole tumor cell-based vaccines are advantageous, because they contain large numbers of antigens, which eliminate the need for targeting the immune response against one antigen at a time. This is important because currently there is little ability to identify specific tumor-associated antigens (TAA) that are useful to induce immune system-mediated tumor regression. Boon et al., *Immunol Today* 1997; 18:267-268. To date, however, autologous whole tumor cell-based vaccines alone have shown only some isolated or marginal successes. Smith et al., supra. As seen below, the marginal success of whole tumor cell-based vaccines likely results from tumor cell mutations that impair their ability to act as antigen presenting cells ("APCs").

Evidence from many tumor immunology laboratories demonstrates that tumor cells persist in part because they have selected a mutation which partially or completely destroys their ability to act as APCs in the process of cytotoxic T lymphocyte CTL generation. Stockert et al., *J. Exp. Med.* 1998; 187: 1349-1354; Sahin et al., *Proc. Natl. Acad. Sci. USA* 1995; 92:11810-11813; Gabrilovich et al., *Nature Med.* 1996; 2:1096-1103; Ishida et al., *J. Immunol.* 1998; 161: 4842-4851. These observations spurred development of strategies that attempt to replace the tumor cell as the APC, rather than trying to boost the tumor's enfeebled antigen presenting process. The best candidate for such a replacement is the dendritic cell ("DC").

DCs are "professional" antigen presenting cells that play a vital role in stimulating immune responses. DCs not only can activate naïve CD4+ T helper cells but also stimulate unprimed CD8+ cytotoxic T lymphocytes. Steinman, R. M. *Annu. Rev. Immunol.* 1991; 9, 271-296; Macatonia, et al., *J. Exp. Med.* 1988; 169, 1255-1264; Mehta-Damani et al., *J. Immunol.* 1994; 153, 996-1003; Porgador et al., *J. Exp. Med.* 1995; 182, 255-260.

Because of these characteristics, DCs have been widely studied as antigen presenting cells for cancer immunotherapy. DCs can be loaded with tumor antigens by pulsing with whole tumor antigens or tumor antigen peptides. (Young et al., *J. Exp. Med.* 1996; 183, 7-11; Mayordoma et al., *Nat. Med.* 1995; 1, 1297-1302; Bakkar et al., *Cancer Res.* 1995; 55, 5330-5334; Flamand et al., *Eur. J. Immunol.* 1994; 24, 605-610; Gong et al., *Gene Ther.* 1997; 4, 1023-1028; Song et al., *J. Exp. Med.* 1997; 186, 1247-1256; Specht et al. *J. Exp. Med.* 1997; 186, 1213-1256.)

Peptide- or tumor lysate-pulsed dendritic cells have been used, for example, to vaccinate melanoma patients. (Rosenberg et al., *Nature Med* 1998; 4: 321-327; Wallack et al., *Cancer* 1995; 75:34-42; Bystryn, *Rec. Results Cancer Res.* 1995; 139:337-348; Mitchell et al., *Semin. Oncol.* 1998; 25: 623-635; Morton et al., *Ann. N.Y. Acad. Sci.* 1993; 690:120-134; Berd et al., *Semin Oncol.* 1998; 25:646-653; Berd et al., *J. Clin. Oncol.* 1997; 15:2359-2370.)

DCs loaded with tumor antigens are able to induce both cellular and humoral, antigen-specific, anti-tumor immune responses. (Shurin, M. R. *Cancer Immunol. Immunother.* 1996; 43, 158-164). This approach, however, is limited to application against tumors expressing known tumor antigens. See, Haigh et al., *Oncology* 1999; 13, 1561-1573. It is worthless for those tumors with no identified tumor antigen, like primary tumors from patients, which constitute most real-world situations. Obviously alternative strategies are needed.

An additional problem with antigen pulsing techniques is that the antigen presenting system of an APC works more effectively and efficiently when the protein/antigen is synthesized inside the cell rather than outside the cell, a substantial drawback to using antigen-pulsed cells. In an effort to avoid this problem, a number of laboratories have attempted to use gene therapy to introduce specific tumor antigens into dendritic cells. (Gong et al., 1997, *Gene Ther.* 4, 1023-28; Song et al., 1997, *J. Exp. Med.* 186: 1247-56; and Specht et al., 1997, supra.). However, this gene therapy approach is also fraught with many disadvantages including: 1) the limited ability to identify all of the important specific tumor antigens, 2) the limited ability to map the genes of the specific tumor antigens, 3) only one or a small number of the known tumor antigen genes can be introduced into the dendritic cell and 4) the process is time-consuming and cumbersome.

On the other hand, fusions between DCs and tumor cells represent an alternative way to produce effective tumor antigen presenting cells by presenting the immune cells with all possible tumor antigens. (Gong et al., *Nat. Med.* 1997; 3: 558-561; Wang et al., *J. Immunol.* 1998; 161, 5516-5524; Lespagnard et al., *Int. J. Cancer* 1998; 76, 250-258; Rowse et al., *Cancer Res.* 1998; 58, 315-321). DCs have been fused with tumor cells and the fused cells efficiently presented tumor antigens to the immune cells and stimulated specific anti-tumor immune responses. (Gong et al.; Wang et al.; Lespagnard et al., all supra).

These fusion schemes, however, rely on selectable markers (gene products which render the cell resistant to specific cell toxins or allow them to grow under certain metabolic conditions) in each of the DCs and the tumor cells to isolate the resultant hybrid. The rare cell fusion products are selected by long-term culture in the presence of both cell toxins where only the fusion product, containing both selectable markers, can survive. Since the introduction and selection schemes using markers requires culture and multiple cell division, they cannot be applied to dendritic cells, because DCs are terminally differentiated, non-dividing cells. Thus, it is no surprise that the previous fusion work relied on well-defined tumor cell lines, bearing such a marker, and DC- and tumor-specific conjugated antibodies, which limits the usefulness of this strategy in cancer treatment.

In summary, the previous cancer-based fusion protocols have the following limitations: 1) they require established tumor cell lines which show specific marker(s); 2) they require both DC and tumor cell specific antibodies to select the fused cells; 3) the selection and expansion of the fused cells takes an impractical amount of time.

The area of preventing transplant rejection using hybrids are even less well-developed than cancer. In fact, no report of such has been found.

Typical approaches to preventing transplant rejection utilize non-selective immunosuppressive drugs that suppress the entire immune system. Abbas et al., CELLULAR AND MOLECULAR IMMUNOLOGY, pp. 347-350. Such approaches have the obvious disadvantage of making the patient more susceptible to disorders that otherwise could have been warded off by an intact immune system.

It has been recognized that at least two interactions must take place in order for an antigen presenting cell to activate a T cell. These interactions are between an antigen-loaded major histocompatibility (MHC) antigen and the T cell receptor, and between certain accessory molecules and their cognate receptors on the T cell. The best studied class of these accessory molecules is B7 (B7.1 and B7.2), which interact with CD28 and CTLA4 on T cells. Abbas et al., supra. Thus, disruption of either the MHC or the accessory interaction should result in a non-response useful, for example, in preventing transplant rejection.

In fact, disruption of B7 interaction not only prevents an immune response, it induces permanent tolerance to any antigen presented during the disruption. Wei, et al., 1996, Stem Cells 14: 232-38. Thus, in the context of transplant rejection, blocking B7 should result in tolerance, preventing rejection. The problem with such an approach, and the likely reason that it has not be attempted clinically, is that tolerance would pertain to any antigen presented during treatment, not just to transplant antigens. In other words, if a patient were exposed to a pathogen during the B7 disruption, the patient's immune system would be rendered tolerant to the pathogen, permanently. This would prevent the patient from warding off the pathogen, having perhaps lethal consequences. Clearly, a more specific approach is needed.

A promising approach takes advantage of antigen presentation by cells that lack accessory molecules, like B7. These cells present antigen in the context of MHC, yet, because they lack the accessory interactions required for activation, they induce tolerance specific to the antigen presented. Thus, it is possible to load these cells, which include immature (naïve) B cells, with a specific antigen, and induce antigen-specific anergy. As with the cancer example described above, this antigen-by-antigen approach does not have the general applicability needed for practical clinical use. A methodology is needed which is applicable to any transplant organ, irrespective of the immunogenic antigens the organ displays.

Neuroblastoma is the most common extracranial solid tumor and the most common tumor occurring during infancy. It also affects young children, and is rarely found in children older than 10 years. Neuroblastoma is an embryonal malignancy of the sympathetic nervous system arising from neuroblasts, which are pluripotent sympathetic cells. In the developing embryo, these cells invaginate, migrate along the neuraxis, and populate the sympathetic ganglia, adrenal medulla, and other sites. The origin and distribution of these cells during fetal development correlate with the sites of primary disease presentation. The location of tumors appears to vary also with the age of the patient. While most neuroblastomas start in the abdomen, a few neuroblastomas develop in the adrenal glands, abdominal ganglias, chest ganglias, neck, spinal chord or the pelvis. Infants suffer more frequently from thoracic and cervical tumors, whereas older children suffer more frequently from abdominal tumors.

Age, stage, and some molecular defects in the tumor cells are the prognostic factors used for risk assessment and treatment strategy. The differences in outcome between patients with neuroblastoma are striking. Infants younger than 1 year have a good prognosis, even in the presence of metastatic disease, whereas older patients with metastatic disease fare poorly, even when treated with aggressive therapy. Unfortunately, approximately 70-80% of patients older than 1 year suffer from metastatic disease, usually to lymph nodes, liver, bone, and bone marrow. Fewer than half of these patients are cured, even with the use of high-dose therapy followed by autologous bone marrow or stem cell rescue.

Treatments for neuroblastoma include surgery, chemotherapy, and/or radiation therapy. Surgery is often used to try to remove as much as possible of the tumor in combination with adjuvant chemotherapy. Chemotherapy becomes the main treatment when the cancer has spread too far to be completely removed by surgery. Most common drugs used in chemotherapy include cyclophosphamide or ifosfamide, cisplatin or carboplatin, vincristine, doxorubicin, etoposide, teniposide and topotecan. A typical combination of drugs commonly used consists of cyclophosphamide, doxorubicin, and vincristine and is alternated with cisplatin plus etoposide. Common side effects include nausea, vomiting, hair loss, mouth sores, depression of the immune system, and bone marrow suppression. In addition, ifosfamide and cyclophosphamide may produce bladder inflammation and blood in the urine, and damage to the kidneys with subsequent loss of salt and minerals in the urine. Cisplatin may produce hearing loss or deafness, kidney damage, and severe and delayed nausea. Doxorubicin (Adriamycin) may cause heart damage if too much of the drug is given and can cause skin damage if the drug should leak out of the vein during administration.

Accordingly, there is a need in the art for improved treatment options for cancer patients, including neuroblastoma patients, and the present invention satisfies that need. There is also a need in the art for rapid methods for inducing and suppressing specific immune responses to whole cells and specific reagents for accomplishing these methods.

SUMMARY OF THE INVENTION

It is, therefore, an object of the invention to provide solutions to the aforementioned deficiencies in the art.

Further to this object, the invention provides a kit useful in preparing hybrid cells. In one aspect, the kit contains at least two essentially endotoxin-free dyes and instructions for preparing hybrid cells from reactant cells by a method that entails contacting reactant cells with one of said dyes, respectively. In another aspect, the kit contains at least two essentially endotoxin-free dyes and an agent that promotes cell fusion. The endotoxin-free dyes are preferably fluorescent dyes, such as cyanine dyes.

Also according to this object of the invention, a hybrid cell preparation is disclosed. In one embodiment, the preparation contains a hybrid cell having no more than n–1 selectable markers, where n represents the number of reactant cells used to form the hybrid and the preparation is substantially free of non-hybrid cells. In another embodiment, the preparation contains a hybrid of a primary tumor cell and an antigen presenting cell. In still another embodiment, the preparation contains a hybrid of a normal cell and an antigen-presenting cell which lacks an accessory factor required to generate a positive immune response. The normal cell may be isolated from a transplant organ. An additional embodiment is a preparation containing a hybrid between a pathogenic cell and an antigen-presenting cell, like a cell from parasite. One hybrid cell preparation is composed of a hybrid cell labeled with at least two different dyes, that are preferably fluorescent, like cyanine dyes. The hybrid cell my be derived from, for example, a dendritic cell or an immature B cell.

Still another aspect of the invention provided in accord with this object is a method of preparing a hybrid cell. One embodiment of the inventive method entails bringing at least two different cells into contact under conditions that promote cell fusion, and then purifying the resultant hybrid without the need for antibiotic or metabolic selection. In one aspect the method is accomplished using fluorescent dyes, like cyanine dyes, and the hybrids are isolated by fluorescence activated cell sorting. The methods can involve fusing reactant cell, like a macrophage, a dendritic cell, and an antigen presenting cell that lacks an accessory factor required to generate a positive immune response, with a second reactant cell, like a tumor cell, a pathogenic cell and a normal cell. The method is preferably accomplished in less than about 48 hours.

In still another aspect, the invention provides a method of treating cancer, that involves providing an inventive hybrid cell preparation that is derived reactant cell that is a cancer cell; and administering the hybrid cell to a cancer patient. The method may include adjunct treatment with a cytokine or lymphokine, like interleukin-2.

In yet another aspect, the invention contemplates a method of treating a disorder associated with the presence of a pathogenic organism that involves providing an inventive hybrid cell preparation that is derived from a cell isolated from said pathogenic organism and administering the cell to a patient. Again, the method may include adjunct treatment with a cytokine or lymphokine, like interleukin-2.

Also in accord with the object of the invention, the invention provides a method of inducing immune tolerance to an antigen that entails providing an inventive hybrid cell preparation that is derived from a cell that expresses an antigen against which immune tolerance is sought and administering said preparation to a patient. The cell against which immune tolerance is sought may be a cell from a transplant organ, where the patient needs an organ transplant.

Further to this object, the invention provides a method for treating cancer in a patient, comprising co-administering to the patient a composition that comprises a primary tumor cell fused to a dendritic cell, and BCG (*Mycobacterium bovis* bacillus Calmette-Guerin). The patient to be treated may have stage I, stage II, stage III or stage IV cancer (staged according to the American Joint Committee on Cancer AJCC Cancer Staging Manual, Sixth Edition, Springer-Verlag New York, N.Y. 2002). Exemplary types of cancer to be treated include, but are not limited to, breast, prostate, bladder, colon, renal, ovarian, skin, lung and melanoma. In one embodiment, the patient has neuroblastoma. In a further embodiment, the method of treating cancer comprises treatment with a population of hybrid cells derived from multiple cancer sites within the patient, in conjunction with BCG therapy. In yet another embodiment, prior to the hybrid cell-BCG combination therapy, the patient has no evidence of disease following surgery, radiation and/or chemotherapy.

In an additional embodiment, the present invention provides a method for increasing survival of a cancer patient, such as a late stage cancer patient, comprising administering to a patient a composition that comprises a hybrid of a primary tumor cell and a dendritic cell, in conjunction with BCG (*Mycobacterium bovis* bacillus Calmette-Guerin) therapy. The patient to be treated may have stage I, stage II, stage III or stage IV cancer. The patient may also be rendered free of evidence of disease (no evidence of disease patient or NED patient) following surgery, radiation and/or chemotherapy. In one aspect of the invention, the cancer patient has breast cancer, prostate cancer, bladder cancer, colon cancer, renal cancer, ovarian cancer, skin cancer, lung cancer or melanoma. In another embodiment, the patient has neuroblastoma.

In a further embodiment, the present invention provides a method for stimulating an immune response in a cancer patient, such as a late stage cancer patient, comprising administering to a patient a composition that comprises a hybrid of a primary tumor cell and a dendritic cell, in conjunction with BCG (*Mycobacterium bovis* bacillus Calmette-Guerin) therapy. The patient to be treated may have stage I, stage II, stage III or stage IV cancer. In one aspect of the invention, the cancer patient has breast cancer, prostate cancer, bladder cancer, colon cancer, renal cancer, ovarian cancer, skin cancer, lung cancer or melanoma. In another embodiment, the patient has neuroblastoma. In one aspect of the invention, the patient has no evidence of disease following surgery, radiation and/or chemotherapy.

Both the foregoing general description and the following brief description of the drawings and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Figure 1:
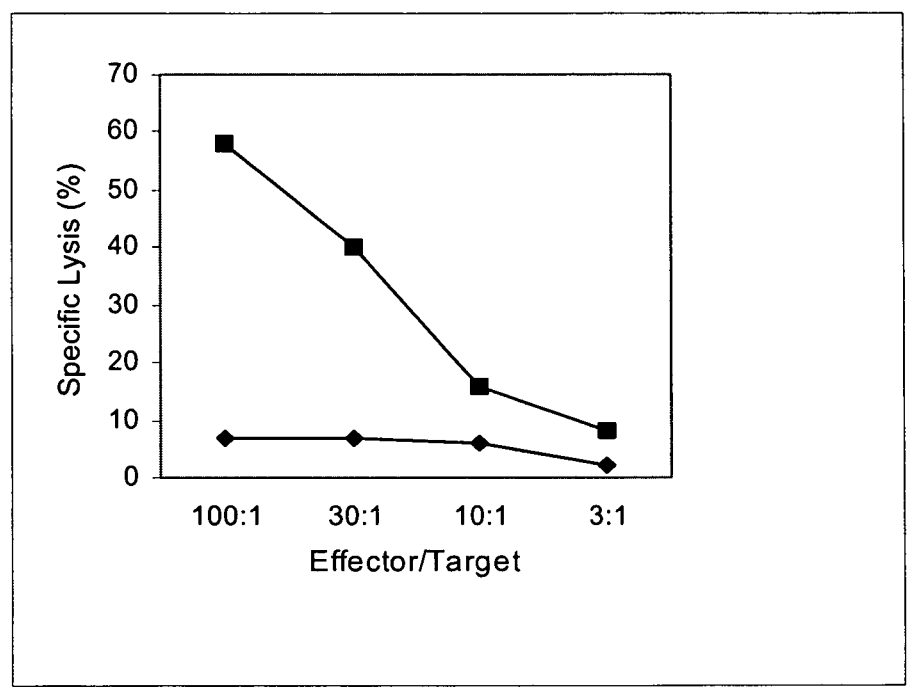
FIG. 1 shows that hybrid cells according to the invention, obtained from the fusion of dendritic cells with cancer cells, are capable of generating a tumor-specific cytotoxic T cell response, which is relevant to in vivo immunotherapy.

In one aspect, the present invention provides a rapid and efficient method of preparing hybrid cells that are useful in a variety of clinical and non-clinical applications. The hybrid cells are particularly useful in treatment regimes that invoke the immune system to treat or prevent disease. For instance, in a preferred embodiment, the inventive hybrid cells are used to treat cancer by fusing a cancer cell to an antigen presenting cell. In another embodiment, the inventive hybrid cells comprise a plasma cell and a cancer cell which, like conventional hybridomas, are useful in preparing monoclonal antibodies. In still another embodiment, the present hybrid cells comprise an antigen presenting cell that lacks an accessory component needed for an immunogenic response and a cell from an organ destined for transplant in a patient. These cells may be used to induce tolerance to the transplant cells, thereby reducing the incidence of transplant rejection. Kits for generating hybrid cells and for practicing the inventive methods also are provided.

The present inventors unexpectedly discovered that hybrid cells of primary tumor cells fused to dendritic cells are exceptionally useful for treating a cancer patient, even a late stage cancer patient, when administered in combination with BCG (*Mycobacterium bovis* bacillus Calmette-Guerin).

Furthermore, even after cancer removal (e.g., tumor resection) through surgery and/or radiation and/or chemotherapy, NED patients are still at a risk for cancer recurrence, since it is believed that cancer cells still exist in the body even though they are not clinically detectable. Therefore, the present invention is also directed to treating a cancer patient who has no clinical evidence of disease with a hybrid cell composition in conjunction with lipopolysaccharide therapy. Indeed, the inventors of this application have surprisingly discovered that the treatment methods of the present invention can decrease risk of cancer recurrence and/or increase survival rate in NED patients.

Tumor Cells

The compositions of the present invention are prepared from tumor cells obtained from surgically resected tumors. The cells are extracted by dissociation, such as by enzymatic dissociation with collagenase and DNase, by mechanical dissociation using a blender, tweezers, mortar and pestle, scalpel blade, or by combination of enzymatic dissociation with mechanical dissociation. Preferably, the tumor cells are rendered replication incompetent by conventional methods, such as irradiation at 5000 rads, prior to fusion with the antigen presenting cells, such that they are incapable of growth and division after administration to the patient.

The tumor cells are derived from the same type of cancer as that needs to be treated, and may be autologous or tissue-type matched, or allogeneic. Preferably, the cells are autologous, e.g., are recognized as "self" by the immune system of the intended recipient.

Antigen Presenting Cells

Antigen presenting cells can be prepared as described in the Examples below. Preferably, the antigen presenting cells are dendritic cells. Dendritic cells are isolated from the patient's peripheral blood mononuclear cells (PBMC's) as described in Romani et al. *Generation of mature dendritic cells from human blood: an improved method with special regard to clinical applicability. J Immunol Methods.* 196(2): 137-151, 1996.

Method of Preparing Hybrid Cells

The hybrid cells of the present invention can be prepared by a rapid, simple to use method that is applicable to fully differentiated, non-dividing cells. The method comprises contacting at least two different cells ("reactant cells") under conditions that promote cell fusion, and then purifying the resultant hybrid ("product cell") without antibiotic or metabolic selection. In general, the purification is accomplished in a relatively short period of time, for example, in less than about 24 to 48 hours, after exposure to conditions that promote cell fusion.

In an exemplary embodiment, the method is accomplished with the aid of at least two different dyes, which can be fluorescent dyes. Thus, the method may entail separately contacting, each with a different dye, the two cell types to be fused. This pre-fusion labeling marks each cell with a different dye, and permits discrimination among each fusion parent cell and the hybrid fusion product: the reactant cells (e.g., tumor cell and dendritic cell) each are stained with one dye, and the product cells are stained with both. This way, the hybrid fusion product may be separated from the reactant cells, for example, by fluorescence activated cell sorting (FACS), magnetic cell sorting, and other cell sorting techniques that do not employ antibiotic or metabolic selection as the means for sorting. The resulting hybrid cell retains the antigen diversity of the tumor reactant cell.

Dyes useful according to the invention have the characteristic of associating with a cell for a time sufficient to detect them in such association. In addition, useful dyes do not substantially diminish cell viability, with greater than about 50% cell viability being preferred. Typically, they are fluorescent dyes. One useful class of dyes comprises the so-called "cyanine" dyes. Cyanine dyes come in a variety of types that fluoresce at different wavelengths such that they can be individually or jointly detected when associated with a cell. Some exemplary cyanine dyes are found in Horan et al., U.S. Pat. No. 4,783,401 (1998), U.S. Pat. No. 4,762,701 (1988) and U.S. Pat. No. 4,859,584 (1989), the structures of which are hereby specifically incorporated by reference.

Two particularly useful cyanine dyes are PKH26-GL and PKH2-GL (Sigma Chemical Co.). These dyes are preferred because they have been widely studied and used. For instance, they have been used in animal studies in vivo for cell trafficking studies. Horan et al., *Nature* 340: 167-168 (1989); Horan et al., *Methods Cell Biol.* 33: 469-490 (1990); Michelson et al., *Proc. Natl. Acad. Sci. USA* 93: 11877-11882 (1996). In laboratory animals these dyes have been shown not to affect cell growth or function and not to migrate from the cells stained with these dyes to other cells (Horan et al., 1989). Thus, these dyes have low toxicity, which is a desirable quality for in vivo applications.

Dyes employed in vivo in accordance with the present invention should be free of endotoxin, as measured, for example, by the Limulus amaebocyte (LAL) assay. Typically, when the measured endotoxin level is less than about 1 ng/μg dye, and preferably less than about 0.1 ng/μg dye, the dye is considered "endotoxin-free."

More generally, the dyes are essentially pyrogen-free, whether pyrogenicity is contributed by endotoxin or other pyrogens. Thus, a dye is considered "essentially pyrogen-free" when the final formulation of hybrid cells labeled with the dye (in a form to be injected into a subject, for example) yields less than about 1 endotoxin unit (EU)/dose, but preferably less than about 0.1 EU/dose, and most preferably less than about 0.05 EU/dose. Toxicity thresholds are informed by the fact that most in vivo methods contemplated herein result in less than about $10^{-8}$ g of these dyes, in association with cells, being introduced into a patient when undertaking the inventive methods of treatment.

Conventional cyanine dye labeling methodologies require the presence of cellular stabilizers (osmolarity-regulating agents), like sugars (e.g., glucose or mannitol), amino acids and/or certain Goods buffers. See, for example, Horan et al., U.S. Pat. No. 4,783,401 (1998). The inventors discovered that dimethyl sulfoxide (DMSO) can substitute for such stabilizers. In particular, DMSO diluted in a standard culture medium may be used as a solvent for cyanine dyes, and it promotes efficient and stable uptake of dye without substantial loss of cell viability. A generally useful range of DMSO concentration is from about 10 to about 50%, but a preferred range is from about 20 to about 40%. The invention therefore also contemplates methods of labeling cells, and corresponding kits, with cyanine dyes using DMSO in place of the conventional stabilizers.

Once the reactant cells are labeled, they are put into contact with one another, under conditions that promote fusion. Such fusion-promoting conditions are well known to the artisan, and typically involve the addition of an agent that promotes cell fusion. These agents are thought to work by a molecular crowding mechanism to concentrate cells to an extent that they are in close enough proximity to cause fusion of cell membranes. While the invention contemplates any agent that meets these characteristics, exemplary useful agents are polymeric compounds, such as polyethylene glycols. An effective amount of such an agent generally will be from about 20% to about 80% (w/v). A preferred range is from about 40% to about 60%, with about 50% being more preferred.

Another suitable method for fusing the reactant cells is by electrofusion, a technique known in the art. Electroporation is the use of electrical fields to induce a reversible breakdown of the cell's lipid bilayer membrane, causing temporary pore formation through which various molecules such as proteins, peptides, DNA or RNA may enter the cell. Electrofusion is the result of an intensive electroporation with membrane breakdown of juxtaposed cells in an inhomogeneous electrical field and consecutive fusion by mutual resealing, Teissie et al., *Biophys J* 74: 1889-1898 (1998). Because the size of the membrane pores is directly related to the strength of the electric field, electrofusion settings are usually characterized by higher field strengths (1000-1875V/cm) than electroporation settings (250-1025V/cm), Shimizu et al, *J Immunother* 27: 265-72 (2004); Kjaergaard et al., *Cell Immunol* 225: 65-74 (2003); Orentas et al., *Cell Immunol* 213: 4-12 (2001); Meldrum et al., *Biochem Biophys Res Comm* 256: 235-239 (1999).

After hybrid cell formation, it is usually beneficial to isolate them from the un-fused reactant cells. In the case of cellular vaccines, for example, this purification substantially increases the potency. Purification may be accomplished by conventional FACS methodologies and the like.

The method explicitly contemplates hybrid cells of higher order, which are fusions between more than two cells. In each case, all that is needed is an additional dye that can serve as a marker for selection of the higher-order hybrid. For example, three different reactant cells labeled with three different dyes are used to form a "tribred," and so on. Thus, as used herein, the term "hybrid cell" contemplates fusions between two or more reactant cells.

Kits of the Invention

The present invention also relates to kits for labeling cells and for preparing hybrid cells. These kits are useful in implementing the inventive method of preparing hybrid cells. A labeling kit, for example, contains at least one dye, and may contain DMSO and instructions for labeling. The inventive hybrid cell preparation kit, comprises at least two essentially endotoxin-free and/or pyrogen-free dyes and instructions for preparing hybrid cells and/or it comprises an agent that promotes cell fusion.

Hybrid Cell Preparations

The invention further contemplates a hybrid cell preparation. In general, the preparation will be substantially free of reactant cells (less than about 50% reactant cells, but preferably less than about 10% to 25% reactant cells, and most preferably less than about 5% reactant cells). The inventive hybrid cells are prepared from reactant cells that may have a selectable marker, but need not. In any event, at least one reactant cell lacks such a marker. Thus, where n represents the number of reactant cells, in most cases, n−1 will represent the maximum number of selectable markers found in the hybrid cell. For example, where two reactant cells fuse to form a hybrid, the hybrid will contain no more than one selectable marker.

The phrase "selectable marker" is used here in its conventional sense, to refer to an antibiotic resistance or a metabolic marker, such as hypoxanthine phosphoribosyl transferase (HPRT), and the like. Selectable markers are endogenously produced, and do not include exogenously added materials, like dyes.

In one embodiment, the inventive hybrid cell preparation comprises a tumor cell and an antigen presenting cell (APC) as reactants. Such hybrids may be used as cellular vaccines to induce an immune response against a disease, such as cancer. The tumor cell may be of any type, including the major cancers, like breast, prostate, ovarian, skin, lung, and the like. The APC preferably is a professional APC, like a macrophage or a dendritic cell. Due to their superior antigen presentation capabilities, dendritic cells are more preferred. Both syngeneic and allogeneic fusions are contemplated as the inventors have discovered using a mouse model that both work equally well.

An additional embodied hybrid comprises a pathogenic cell and an APC. These hybrids also are useful as cellular vaccines. Again, antigen presenting cells, and dendritic cells, in particular, are favored. The pathogenic cell, on the other hand, may be of virtually any type. For example, it may be a bacterial cell (*Helicobacter*, etc.) that has had its cell wall removed. The pathogenic cell may be a fungal cell, like *Candida, Cryptococcus, Aspergillus* and *Alternaria*.

The pathogenic cell also may be a parasitic cell from, for example, trypanosomal parasites, amoebic parasites, miscellaneous protozoans, nematodes, trematodes and cestodes. Exemplary genera include: *Plasmodium; Leishmania; Trypanosoma; Entamoeba; Naeglaria; Acanthamoeba; Dientamoeba; Toxoplasma; Pneumocystis; Babesia; Isospora; Cryptosporidium; Cyclospora; Giardia; Balantidium; Blastocystis; Microsporidia; Sarcocystis; Wuchereria; Brugia; Onchocerca; Loa; Tetrapetalonema; Mansonella; Dirofi-*

*laria; Ascaris* (roundworm); *Necator* (hookworm); *Ancylostoma* (hookworm); *Strongyloides* (threadworm); *Enterobius* (pinworm); *Trichuris* (whipworm); *Trichostrongylus; Capillaria; Trichinella; Anasakis; Pseudoterranova; Dracunculus; Schistosoma; Clonorchis; Paragonimus; Opisthorchis; Fasciola; Metagonimus; Heterophyes; Fasciolopis; Taenia; Hymenolepis; Diphyllobothrium; Spirometra*; and *Echinococcus*.

In another embodiment, the inventive hybrid cell preparation comprises a target cell against which immune tolerance is desired and an antigen presenting cell that lacks an accessory factor needed for an immunogenic response. Typically these APCs lack B7 (e.g., B7.1 or B7.2); exemplary cells are naïve, immature B cells and fibroblasts, but any cell capable of presenting antigen (having MHC molecules), yet lacking an accessory molecule, will suffice. In the case of B7, specific antibodies are known, and the artisan will be well apprised of methods to ascertain whether any particular cell type lacks B7. Naïve B cells are preferred because they express high levels of MHC molecules and all the adhesive molecules known in the art to be necessary for efficient cell-cell contact.

In any event, the resultant hybrids have the ability to present antigen to the immune system, since they bear class I and class II MHC molecules, yet they will not have the ability to activate the immune system, since they do not have the necessary accessory markers, like B7 (CD28 or FLTA4 ligands). Thus, instead of inducing an immune response, these hybrids will induce apoptotic clearance, thereby rendering the immune system tolerant to the target cell antigens presented by these hybrids. Such immune cell hybrids are useful in treating autoimmune disorders like transplant rejection.

The APC preferably is a professional APC, like a macrophage or a dendritic cell. Due to their superior antigen presentation capabilities, dendritic cells are preferred. Both autologous and allogeneic fusions are contemplated. Ultimately, the antigen diversity of the starting tumor cell population is maintained in the resultant hybrid cell population.

The inventive hybrid cell preparation may be made using a combination of dyes, as detailed above. Thus, the inventive hybrid cell may be labeled with at least two different dyes. These dyes are preferably fluorescent and, again, cyanine dyes are favored. Alternatively, hybrid cells may be prepared, for example, using cell surface markers differentially expressed on the reactant cells and corresponding antibodies to them. The antibodies may be used to pan sequentially for each marker.

BCG Preparation

The invention further contemplates a BCG (*Mycobacterium bovis* bacillus Calmette-Guerin) preparation, which is an inactivated form of the bacterium *Mycobacterium bovis*. Safe and effective BCG preparations are commercially available.

Methods of Treatment

Multiple factors determine the survival rate of a patient with cancer, including tumor size and thickness, extension, lymph node status, and metastatic status. The patient's prognosis is also affected by other factors, such as age of the patient and health-related factors. Cancer staging is important for identifying appropriate treatment options for a particular cancer and individual. In 1998, the American Joint Committee on Cancer (AJCC), in collaboration with the National Cancer Institute Surveillance, Epidemiology and End Results Program (NCI-SEER); Centers for Disease Control and Prevention National Program of Cancer Registries (CDC/NPCR); National Cancer Registrars Association (NCRA); North American Association of Central Cancer Registries (NAACCR); and American College of Surgeons (ACOS) Commission on Cancer (CoC), began addressing the discrepancies in staging guidelines among the three major staging systems used in the United States, and developing a unified system between the tumor-lymph nodes-metastasis (TNM) staging system of the AJCC and the SEER Summary Staging System. The Collaborative Staging System is based on and compatible with the terminology and staging used in the sixth edition of the *AJCC Cancer Staging Manual*, published in 2002.

The AJCC TNM staging system uses three basic characteristics of cancer that are then grouped into stage categories to determine an overall degree of severity for the patient's cancer. "T" describes the size and the extent of the primary tumor. The T component is accompanied by a number 1-4 that further identifies the size and local spread of the tumor. A higher number indicates either a larger tumor or one that has a greater effect on the surrounding tissues. "N" describes the absence or presence and extent of regional lymph node metastasis, the number of nodes involved and their size. A number from 0 to 2 indicates the level of lymph node involvement; and a higher number indicates a more severe condition. "M" describes the absence or presence of distant metastasis. The stage categories range from Stage 0 through Stage IV, with the lower staging number corresponding to a less severe cancer. This simplified staging method helps determining the best course of treatment and provides an indication of the patient's prognosis.

The SEER Extent of Disease (EOD) coding system is a five-field, 10 digit system that provides information on the tumor size, extension of the primary tumor, regional lymph node involvement, number of pathologically reviewed regional lymph nodes that are positive, and number of pathologically examined regional lymph nodes.

The present inventors surprisingly discovered that hybrid cells, in combination with BCG therapy, are exceptionally useful in treating a cancer patient, even a late stage cancer patient.

In one aspect of the invention, the patient has a solid tumor cancer, such as renal cancer, ovarian cancer, lung cancer, breast cancer, prostate cancer, bladder cancer, colon cancer, or skin cancer, such as melanoma. In another aspect of the invention, the patient has neuroblastoma. In yet another aspect of the invention, the patient has stage II neuroblastoma (stage IIA or IIB), stage III neuroblastoma or metastatic stage IV neuroblastoma (staged according the International Neuroblastoma Staging System, INSS).

Removal of all identifiable cancer growths, with multiple resections at multiple sites of disease, if necessary, may render the patient free of evidence of disease (NED) even at a late stage, such as stage IV. Thus, in this patient population, cancer removal followed by hybrid cells treatment in conjunction with BCG therapy, can decrease the risk of cancer recurrence and increase patient survival rate. This method improves the likelihood of a favorable long-term prognosis in patients with stage I-NED, stage II-NED, stage III-NED, and even stage IV-NED cancer. The cancer can be any solid tumor cancer, including but not limited to, renal cancer, ovarian cancer, lung cancer, breast cancer, prostate cancer, bladder cancer, colon cancer, skin cancer, such as melanoma, or neuroblastoma. Accordingly, the hybrid cell composition of the invention can be administered to a patient who has no clinical evidence of disease (NED) as a result of, for example, surgery (including surgical resection of tumor), and/or radiation therapy and/or chemotherapy (including antimetabolites, alkylating agents, immunomodulatory agents, various natural products (e.g., vinca alkaloids, epipodophyllotoxins, antibiotics, and amino acid-depleting enzymes), antibodies, hormones and hormone antagonists), regardless of the stage of cancer.

The method of treatment according to the present invention comprises co-administering to a cancer patient a composition comprising a non-proliferative hybrid between a first reactant cell and a second reactant cell, typically an antigen-presenting cell, and BCG. For the purposes of the present invention, the term "patient" denotes an animal. In a preferred aspect of the invention, the patient is a mammal. In the most preferred aspect of the invention, the mammal is a human.

The first reactant cell is one against which an immune response is sought, such as a primary tumor cell. Preferably, the treatment method involves co-administering a composition comprising a hybrid cell prepared by fusing a first reactant cell isolated from a patient, such as a tumor cell, with an antigen presenting cell, such as a dendritic cell. In a preferred embodiment, the hybrid cell is prepared by fusing a tumor cell from a neuroblastoma isolated from a patient having neuroblastoma, with a dendritic cell obtained from the peripheral blood of the patient. Preferably, the tumor reactant cells are lethally irradiated prior to fusion. Irradiation of the tumor cells does not prevent efficient presentation of the tumor antigen(s) by the resultant hybrid cell. Both autologous and allogeneic fusions are contemplated. The non-proliferative hybrid cell thus obtained from the fusion of the tumor cells with their dendritic cells are called dendritomas. A pharmaceutically-acceptable dendritoma vaccine, comprising the hybrid cells thus produced and an excipient, such as phosphate buffered saline (PBS), is then co-administered subcutaneously, preferably near a lymph node, to a cancer patient, in conjunction with the BCG preparation.

In one embodiment, the dendritoma vaccine and the BCG preparation are not mixed but are co-administered. For the purposes of the present invention, the terms "co-administering" and "co-administration" refer to a process by which a BCG preparation according to the invention is administered to the cancer patient subcutaneously, simultaneously or sequentially with respect to the administration of the dendritoma vaccine. The term "simultaneous" denotes the simultaneous administration of the dendritoma vaccine and the lipopolysaccharide to the patient. In a preferred embodiment, administration of the BCG preparation to the patient is sequential to the administration of the dendritoma vaccine, i.e., the BCG is preferably administered after the dendritoma vaccine, such as about 5 minutes, about 10 minutes, about 15 minutes, about 20 minutes, about 25 minutes, about 30 minutes, or about 45 minutes after administration of the dendritoma vaccine. In this context, the term "about" refers to ±1 minute.

In another embodiment, the dendritoma vaccine and BCG are formulated together and administered to the cancer patient.

Vaccine Formulations

The dendritoma vaccine compositions of the invention are administered in a mixture or in combination with a pharmaceutically-acceptable carrier, such as phosphate buffered saline (PBS). After the initial vaccination, the patient may be revaccinated every 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, but preferably every 4-6 weeks. For example, the patient may be revaccinated every 4 weeks, receiving a maximum of 6 vaccinations, depending on the total number of dendritomas obtained. Dosages of the dendritoma vaccine may be determined by the artisan skilled in the art and may be based on the patient's clinical condition, as well as potency of the vaccine material, use and type of vaccine adjuvant or formulation, how different the vaccine is from the host, route and schedule of administration, immune status of the recipient, body weight, etc. In a preferred embodiment of the invention, the composition comprises a dendritoma vaccine comprising at least about 100,000 dendritomas in a pharmaceutically acceptable carrier or diluent, such as, but not limited to, phosphate buffered saline (PBS). The dendritomas may be administered by subcutaneous injection into an area of lymph nodes in the axilla or inguinal area of the patient. The injection site may be rotated to avoid injection in the same lymph node bed on two consecutive administrations.

In one embodiment, the BCG and dendritoma vaccine are formulated together. In another embodiment, the BCG preparation of the invention is administered subcutaneously within about 5 minutes, 10 minutes, 15 minutes, 20 minutes, 25 minutes, 30 minutes, or 45 minutes of the administration after each dose of the dendritoma vaccine. The dosage of BCG administered after the initial vaccination may be determined by the artisan skilled in the art based upon the detection of changes in the immunodeficiency panel and in the number of T cells expressing interferon γ (IFN-γ) in the patient, or the reaction to the TB skin test administered to the patient prior to administration, as depicted in Table 1 below:

TABLE 1

Dosage of BCG After Initial Vaccination-

| TB skin test result | Dermatologic reaction | BCG dose |
|---|---|---|
| Negative | None | 1,000,000 Units |
| Positive | <10 mm In Duration | 250,000 Units |
| Positive | ≥10 mm In Duration, | 20,000 Units |

BCG preparations for second administration to the patient comprise at least about 10,000 units, preferably at least about 20,000 units, more preferably at least about 100,000 units, still more preferably at least about 250,000 units, even more preferably at least about 500,000 units, and most preferably at least about 1,000,000 units, depending on whether the initial injection produces ulceration at the injection site, in which case the BCG dose is reduced to 50% of the initial dose. BCG preparations for subsequent administrations may comprise from about 0.0 to about 1,000,000 units, and may be determined by the artisan skilled in the art based on the patient's reaction to the first and second administration of the BCG preparation. If the initial BCG administration produces ulceration at the injection site, and ulceration at the site of injection occurs after the dosage of BCG is decreased by 50% for the second administration, the dendritoma vaccine is administered alone, without BCG, on all subsequent injections.

Clinical Response

The patient's response to the methods of treatment of the present invention may be evaluated according to standard criteria based on target lesions and non-target lesions. Target lesions are defined as all measurable lesions up to a maximum of 10 lesions representative of all involved organs, and are measured and recorded at baseline. Non-target lesions are all other lesions, or sites of disease, recorded, but not measured, at baseline as present or absent. In the evaluation of target lesions, a complete response (CR) indicates complete disappearance of all target lesions; a partial response (PR) indicates at least about 30% reduction in the sum of the longest diameter (LD) target lesions taking as reference the baseline LD; a stable disease (SD) indicates neither sufficient shrinkage in target lesions to qualify for partial response, nor sufficient increase in target lesions to qualify for progressive disease (PD), when considering the smallest sum LD recorded since the beginning of treatment; and a progressive disease (PD) indicates at least a 20% increase in the sum of the LD of target lesions when considering the smallest sum LD recorded since the beginning of treatment, or the appearance of one or more new lesions. In the evaluation of non-target lesions, a complete response indicates the disappearance of all non-target lesions; a non-complete response (non-CR) or non-progressive disease (non-PD) indicates the persistence of one or more non-target lesions; and a progressive disease (PD) indicates the appearance of one or more new lesions or the unequivocal progression of existing non-target lesions.

The best overall response is the best response recorded for the start of the treatment until disease progression/recurrence (taking as reference for the progressive disease the smallest measurements recorded since the treatment started) The patient's best response assignment will depend on the achievement of both measurement and confirmation. The evaluation of the best overall response is summarized in Table 2.

TABLE 2

Evaluation of best overall response*

| Target Lesions | Non-Target Lesions | New Lesions | Overall Response |
|---|---|---|---|
| CR | CR | No | CR |
| CR | Incomplete response/SD | No | PR |
| PR | Non-PD | No | PR |
| SD | Non-PD | No | SD |
| PD | Any | Yes or No | PD |
| Any | PD | Yes or No | PD |
| Any | Any | Yes | PD |

*CR, complete response;
PR, partial response;
SD, stable disease;
PD, progressive disease.

To be assigned the status of partial response or complete response, the changes in tumor measurement must be confirmed by repeat assessments performed ≥4 weeks after the criteria for the response are first met. If the patient has no evidence of disease at Day 0, time to recurrence will be evaluated and any recurrence will be classified as progression of disease. Preferably, upon treatment with the dendritoma vaccine and BCG therapy of the present invention, the patient has at least a partial response, and most preferably the patient has complete response to the therapy.

Although the patient may have a "mixed response," the treatment method may nevertheless still be considered effective. A treatment regimen is considered "effective" if it can prolong the time to relapse or increase a patient's overall survival beyond the patient's expected age of survival, given the stage and type of cancer immediately prior to the treatment according to the present invention. For example, the method of treatment of the present invention is useful in increasing survival of a patient having late stage cancer by at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 1 year, at least about 1.5 years, at least about 2 years, at least about 2.5 years, at least about 3 years, at least about 3.5 years, at least about 4 years, at least about 4.5 years, at least about 5 years, at least about 6 years, at least about 7 years, at least about 8 years, at least about 9 years, at least about 10 years, etc.

The foregoing detailed description and the following examples are offered for illustrative purposes and are not meant to be limiting. The artisan will recognize that there are additional embodiments that fall within the invention, but are not described with particularity. All references identified herein, including U.S. patents, are hereby expressly incorporated by reference.

EXAMPLES

Example 1

Animal Studies

This example demonstrates the preparation of certain hybrids between cancer cells and dendritic cells, called dendritomas. These hybrids were used as a cellular vaccine to prevent cancer in a murine metastatic cancer model system.

To prepare dendritic cells from bone marrow, the appropriate number of female C57BL/6J mice to support later dendritoma injections (two mice for every one mouse to be injected) were sacrificed. The femur and tibia of both hind legs were removed from each mouse. Bone marrow was flushed out of the bones using a syringe containing RPMI 1640 with 25 mM Hepes (Gibco BRL). The media containing the bone marrow was filtered through a 40 μm cell strainer into a 50 ml conical centrifuge tube. The bone marrow cells were pelleted by centrifugation at 1500 rpm for five minutes. After removing the supernatant, the tube was gently tapped to loosen the cell pellet. Red blood cell lysis was achieved by adding 5 ml/mouse of ACK Lysing Solution (0.15 M $NH_4Cl$, 1 mM $KHCO_3$, 0.1 mM $Na_2EDTA$, pH 7.3) and incubating at room temperature for five minutes. The cells were pelleted by centrifugation at 1500 rpm for five minutes. The supernatant was removed, and the cells were gently resuspended in 10 ml/mouse of complete DC media (RPMI 1640, 10% fetal bovine serum (FBS), 100 μg/ml gentamicin, 10 ng/ml GM-CSF, 10 ng/ml IL-4). The cells were plated into two wells/mouse of a six well tissue culture plate. After incubating the cultures overnight at 37° C., 5% $CO_2$, the floating cells were removed from each culture. Adherent cells were washed twice with 1× Phosphate Buffered Saline (PBS). Each well of cells was fed 5 ml of complete DC media. The cultures were incubated for 48 hours at 37° C., 5% $CO_2$. The dendritic cells were harvested from the 6 well plate by removing the supernatant containing the cells to a 15 ml conical centrifuge tube. Each well was washed twice with 3 ml of 1×PBS. The cells were lightly trypsinized by adding 1 ml of 0.25% Trypsin/EDTA (Gibco BRL) to each well. After rocking the plate to cover the entire surface, the trypsin solution was quickly removed from the plate. The plate was lightly tapped to remove any loosely attaching cells. These cells were resuspended in 2 ml of complete DC media and added to the 15 ml tube. The cells were pelleted by centrifugation at 1500 rpm for five minutes. After resuspending the cells in 10 ml of complete DC media, a cell count was taken.

B16F0 murine melanoma cells were obtained from the ATCC(CRL-6322) and cultured using standard tissue culture techniques. When the cells were ready for use, they were trypsinized using 0.25% Trypsin/EDTA. After taking a cell count the number of cells needed for experimentation were pelleted by centrifugation at 1500 rpm for five minutes. The remaining cells were cultured for later use.

For general cell membrane labeling of murine dendritic cells and B16F0 melanoma cells, a commercial fluorescent cell linker kit was used. The dendritic cells were labeled fluorescent green using Sigma stock number PKH2-GL; the B16F0 melanoma cells were labeled fluorescent red using Sigma stock number PKH26-GL. The staining procedure was performed at 25° C. The cells to be stained were washed with serum-free media. The cell suspension was centrifuged at 400 g for five minutes to obtain a loose pellet. Supernatant was removed leaving less than 25 µl of medium on the pellet. The pellet was resuspended by tapping the tube, and 1 ml of Diluent A or C for green or red staining respectively was added to resuspend the cells. Immediately prior to staining, $4 \times 10^{-6}$ molar dyes (2×) were prepared with Diluent A or C in polypropylene tubes. To minimize ethanol effects, the amount of dye added was less than 1% of the individual sample volume. The cells in the diluent were rapidly added into 1 ml of 2× dye. The cells and dye were immediately mixed by gentle pipetting. The mixture was then incubated at 25° C. for five minutes. The staining process was stopped by adding an equal volume of FBS and incubating for one minute. The stained cells were diluted with equal volume of complete culture medium. Stained cells were removed from the staining solution by centrifuging at 400 g for 10 minutes. After a total of three washes, the cells were resuspended in complete medium at a proper concentration. Efficiency of staining was monitored by fluorescent microscopy.

Prior to the fusion process, the red fluorescently stained B16F0 murine melanoma cells were irradiated with 5,000 rads. Murine dendritic cells and B16F0 melanoma cells were fused together by mixing the two cell types at a 1:1 ratio in a 50 ml conical centrifuge tube. The tube was filled with serum-free RPMI 1640 with 25 mM Hepes. The cell mixture was centrifuged at 1500 rpm for five minutes at room temperature. During the fusion process, all solutions as well as the tube in which the fusion was performed were kept at 37° C. using double-beaker water baths. The supernatant from the mixed cell pellet was aspirated and discarded. Using a 1 ml serological pipet, 1 ml of prewarmed 50% PEG/DMSO (Sigma), which contained 50% PEG and 10% DMSO in PBS ($Ca^{++}$- and $Mg^{++}$-free), was added to the mixed cell pellet drop-by-drop over one minute, stirring the cells with the pipet tip after each drop. The mixture was stirred for an additional minute with the pipet.

Using a clean 2 ml serological pipet, 2 ml of prewarmed serum free RPMI 1640 with 25 mM Hepes was added to the cell mixture drop-by-drop over two minutes, stirring after each drop. With a 10 ml serological pipet, 7 ml of prewarmed serum free RPMI 1640 with 25 mM Hepes was added drop-by-drop over two to three minutes. The cells were pelleted by centrifugation at 1500 rpm for five minutes at room temperature. The supernatant was discarded, and the tube was placed back into the beaker water bath. With a clean 10 ml serological pipet, the cell pellet was resuspended in 10 ml of complete DC media by forcefully discharging about 3 ml of media onto the pellet and then gently adding the remaining media. The resuspended cells were put into a T75 tissue culture flask. The instant dendritomas (fused dendritic cells with melanoma cells) were incubated overnight at 37° C., 5% $CO_2$. A drop of the cells was placed on a slide and evaluated by fluorescent microscopy to ensure the occurrence of fusion.

The instant dendritomas were removed from the tissue culture flask by saving the supernatant containing the cells as well as lightly trypsinizing the adherent cells as previously described. The cells were pelleted by centrifugation at 1500 rpm for five minutes. The cell pellet was resuspended in 2 ml of 1×PBS and put into a sterile, polystyrene, round bottom, 12×75 mm Falcon tube. After centrifuging the cells at 1500 rpm for five minutes, they were resuspended in 1 ml of 1×PBS. The instant dendritomas were sorted out based on dual green and red fluorescence using a FACS Caliber (Becton Dickinson), using standard methods.

The sorted cells were pelleted by centrifugation at 2000 rpm for 30 minutes. After removing the supernatant, the cells were resuspended at a concentration of 50,000 cells/0.5 ml 1×PBS. A drop of the cells was placed on a slide and evaluated by fluorescent microscopy to ensure the general purity of the sort.

Three days prior to the fusion process, female C57BL/6J mice were challenged with $0.75 \times 10^6$ B16F0 melanoma cells in 0.4 ml 1×PBS by intravenous injection. Once the instant dendritomas were pelleted and resuspended, each mouse was injected intravenously with 50,000 cells. The mice were monitored up to four weeks for pulmonary metastasis.

At the end of four weeks, the mice were sacrificed and the metastases were counted. Each of the four control animals, which were not treated with the instant dendritomas, had greater that 50 tumors. On the other hand, only one of the treated animals had measurable metastases. These data indicate that the hybrid cells are effective in treating cancer in a proven animal model system. The data are compiled in the following Table 3.

TABLE 3

Number of Metastases in Control and Treated Mice

| GROUP | Number of Metastases (including tumors at non-lung sites) |
|---|---|
| Control | |
| A | >50 |
| B | >50 |
| C | >50 |
| D | >50 |
| Experimental | |
| A | 0 |
| B | 3 |
| C | 0 |
| D | 0 |

Example 2

Method of Producing Hybrid Cells

A. Collection and Processing of Autologous Serum

Figure 3:
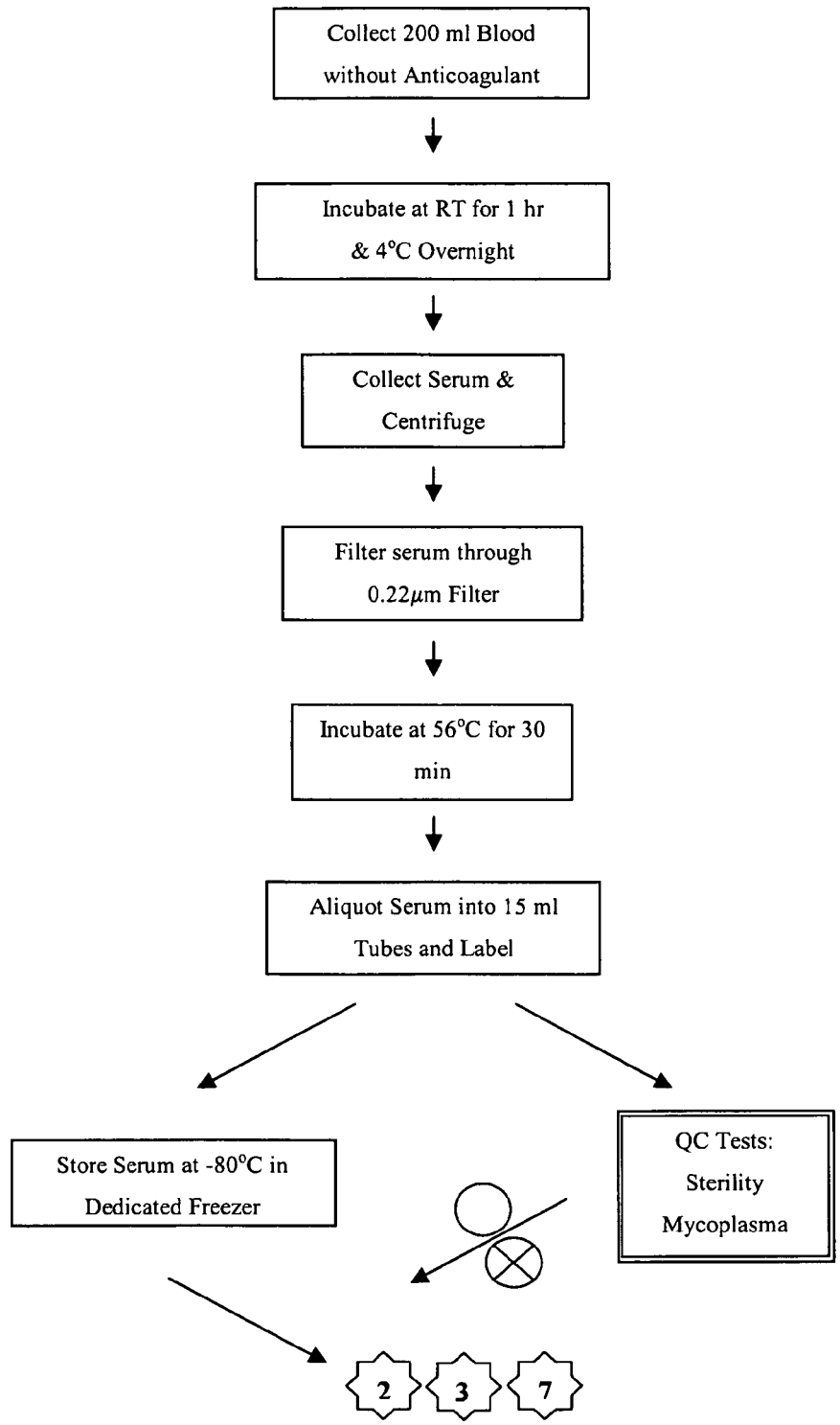
FIG. 3 is a flow diagram representing the process for manufacturing autologous serum.

Blood is collected from the patient into a dry blood collection bag. Autologous serum is used for culture of the patient's dendritic cells and cryopreservation of the patient's tumor cells and dendritomas. Serum is isolated using standard procedures from 200 ml of peripheral blood collected without anticoagulants. The blood is allowed to clot at room temperature and then put in the refrigerator overnight. The serum is then removed from the clotted blood and centrifuged. The supernatant is filtered through a 0.22 µm filter. The serum is then inactivated by incubating at 56° C. for 30 minutes, aliquoted into 15 ml tubes, labeled and stored at −80° C. A small amount of the serum sample is also used for quality control testing. This autologous serum comprises 10% by volume of the culture media used for the culture of the patient's dendritic cells and the freezing medium for cryopreservation of tumor cells and dendritomas. If needed, additional serum may be obtained during additional collection procedures. A flow diagram representing the process for manufacturing autologous serum is shown in FIG. 3.

B. Tumor Cell Preparation from Surgically Excised Tissue

Tumor specimens are collected from patients undergoing biopsy or other appropriate procedure and further processed. Quality control evaluation of the tumor samples includes label verification and visual inspection of the container.

A tumor section is obtained at the time of biopsy or excisional resection before the specimen is sent to the pathology laboratory. After separating fat and necrotic tissue away from the tumor tissue, the tumor is cut into small pieces and put into a T75 flask. Twenty milliliters of digestion medium (RPMI-1640, 0.5 U/ml collagenase, 50 µg/ml Pulmozyme) are added to the flask. This solution is then rocked for 1-4 hours at 37° C. The cell suspension is then collected and filtered through a 40 µm cell strainer (Falcon Cat#2340). The cells are pelleted at 500 g for 5 minutes at room temperature. 15 to 40 ml of ACK lysing solution (Cambrex) is added to the cell pellet and incubated for 5 minutes at room temperature to lyse the red blood cells.

Figure 4:
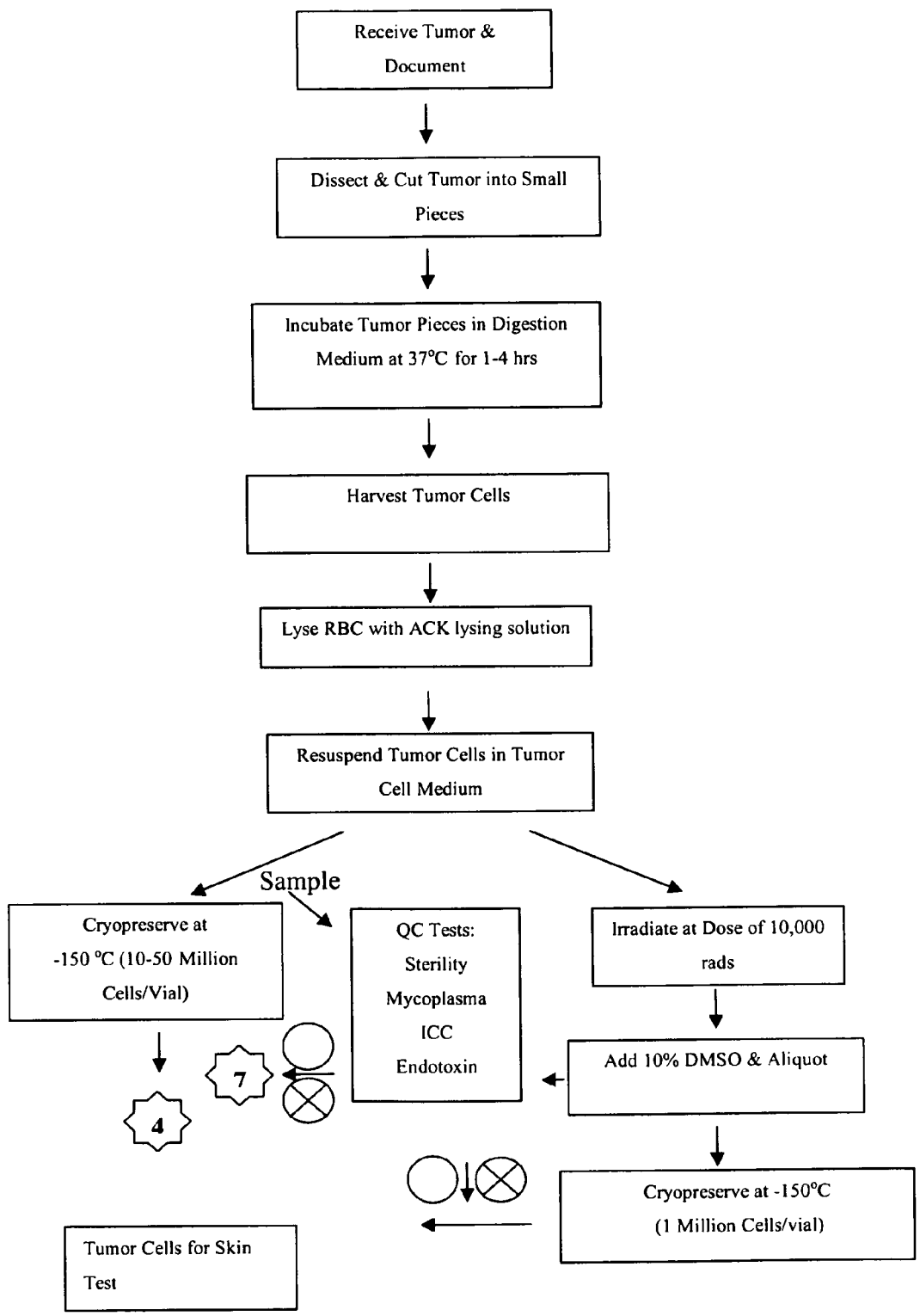
FIG. 4 is a flow diagram representing the tumor specimen processing.

For the tumor cell skin test, 8 million tumor cells are collected, washed, resuspended in 7.2 ml medium (80% RPMI-1640 and 10% autologous serum), and irradiated with 10,000 rads. After irradiation and the addition of 0.8 ml DMSO, the cells are aliquoted ($1 \times 10^6$ cells/vial) and cryopreserved. At the same time, a sample is taken for lot-release testing. At the time of skin testing, the tumor cells are thawed and transferred to a 1 cc syringe for intradermal injection. The remaining tumor cells are immediately cryopreserved using a similar procedure, but with higher concentrations (10-50 million cells/ml). A quality control sample is collected before the cryopreservation. If the number of tumor cells is insufficient to manufacture the dendritoma vaccine, additional tissue may be obtained, if possible, or patient may be withdrawn from study. FIG. 4 provides an overview of the tumor specimen processing.

C. Dendritic Cell Generation

Figure 5:
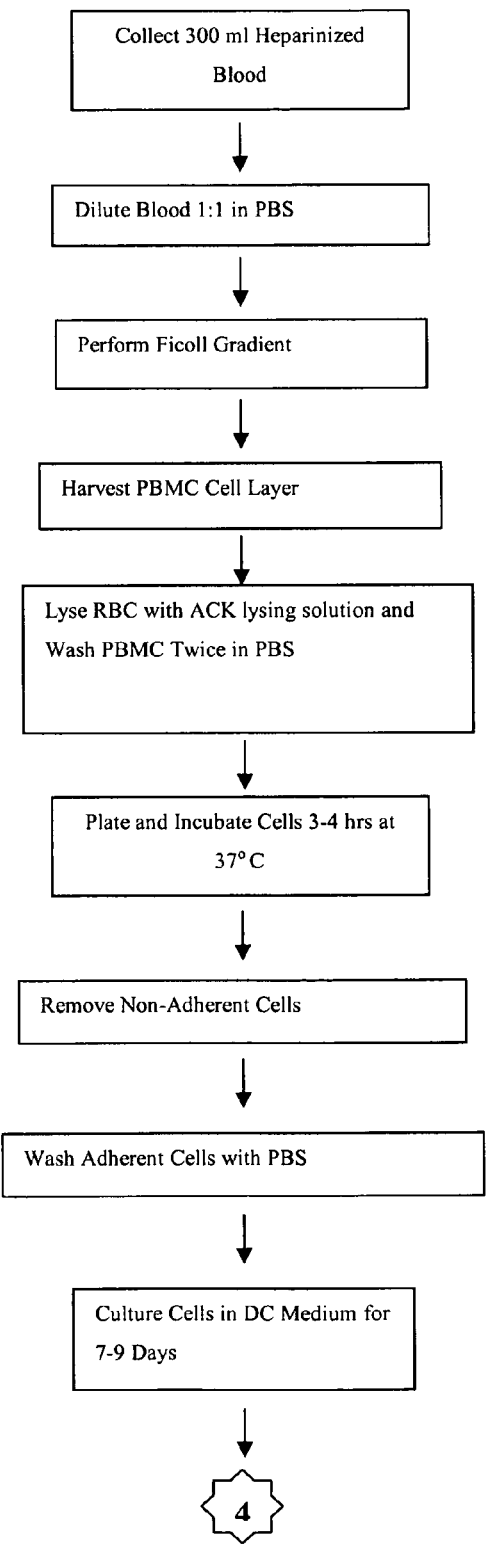
FIG. 5 is a flow diagram representing the process for the generation of dendritic cells.

Dendritic cells are generated from the patient's peripheral blood monocytes (PBMCs). Three hundred milliliters of sodium heparinized peripheral blood are collected from the patient and diluted 1:1 with 1×PBS. Then, 120 ml of the diluted blood are layered over 85 ml of room temperature Ficoll-Paque Plus in six 230 ml centrifuge bottles, and centrifuged at 500 g for 30 minutes at room temperature. The PBMC layers are removed from the Ficoll gradients, and placed into clean 250 ml centrifuge tubes. Four volumes of 1×PBS are added and the tubes are inverted to mix. The PBMCs are then centrifuged at 500 g at room temperature for 10 minutes. Ten ml of 1×PBS are added into each tube, and the cells are resuspended and pooled into 1 tube. The PBMCs are again centrifuged at 500 g at room temperature for 10 minutes. The cells are resuspended in 20 to 40 ml of ACK lysing solution (Cambrex) and incubated at room temperature for 5 minutes. The cells are then centrifuged again. The PBMCs are resuspended in 50 ml of RPMI 1640+25 mM Hepes media. The cells are then placed onto 100 mm tissue culture plates, swirled, and incubated at 37° C. for 3 to 4 hours. The non-adherent cells are then removed. Ten ml of 1×PBS are added, the plate is swirled, and the PBS is removed. Afterwards, 10 ml of complete DC media (RPMI 1640+10% autologous patient serum+800 U/ml GM-CSF+ 1000 U/ml IL-4+100/g/ml gentamicin) is added to each plate. The plates are then incubated at 37° C., 5% $CO_2$ for 7-10 days to generate dendritic cells. FIG. 5 provides an overview of the process generating dendritic cells.

Example 3

Method of Manufacturing the Dendritoma Vaccine

The manufacturing of the dendritoma vaccine can be divided into several phases: A. fluorescent dye staining; B. fusion of dendritic cells and tumor cells; C. purification; and D. final product formulation. These stages are shown below.

A. Fluorescent Dye Staining of Dendritic Cells and Tumor Cells

The fluorescent dyes used in dendritoma production are PKH26-GL and PKH2-GL from Sigma. These dyes have been used in animal studies in vivo for cell trafficking studies. In laboratory animals these dyes have been shown not to affect cell growth or function and not to migrate from stained cells to other cells. In the clinical investigation, less than $10^{-14}$ g of these dyes associated with the dendritoma vaccines are introduced into the patient.

Figure 6:
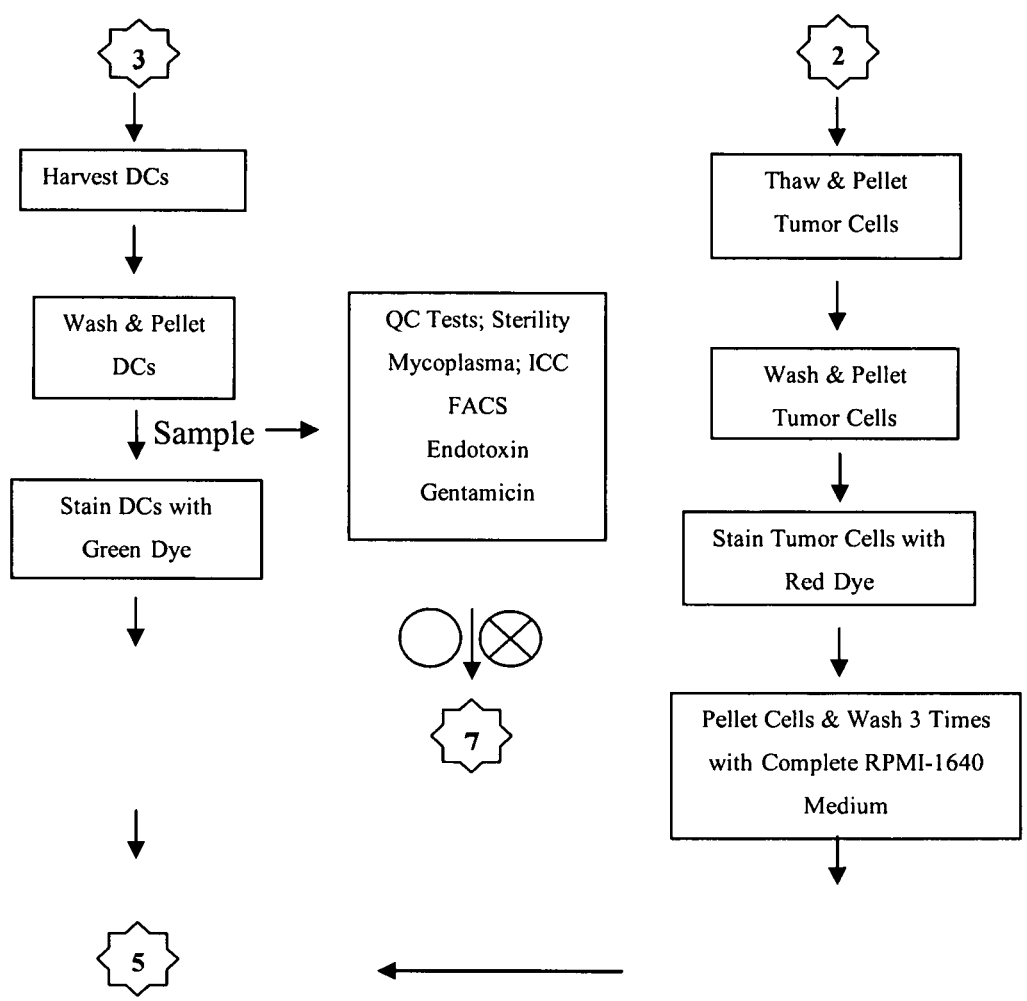
FIG. 6 is a flow diagram representing the procedure for fluorescent dye staining of dendritic cells and tumor cells.

Dendritic cells generated from patient's blood are stained fluorescent green and tumor cells from the same patient are stained fluorescent red. After irradiation, the red tumor cells are fused with the green dendritic cells using PEG. Hybrid formation by cell fusion using PEG as fusing agent is routine procedure. The procedure outlined below is a variation of the one reported by Prado et al. for PEG mediated fusion of somatic cells in monolayers. The hybrid cells which retain both the character of the tumor cells as well as the ability of the dendritic cells to act as an effective antigen presenting cell (APC), are then purified by FACS according to their unique fluorescent color. FIG. 6 shows a flow diagram representing the procedure for fluorescent dye staining of dendritic cells and tumor cells.

B. Dendritic Cells and Tumor Cells Fusion

The green dendritic cells are mixed with the red tumor cells irradiated with a single dose of 5000 rads sufficient to render the cells replication incompetent at ratios of 1:1 to 5:1 or 1:1 to 1:5 in a 50 ml conical centrifuge tube. The tube is filled with serum-free RPMI 1640 medium. The cell mixture is centrifuged for 5 minutes at 500 g. While the cells are being centrifuged, two 37° C. double-beaker water baths are prepared in the laminar flow hood by placing a 250-ml beaker containing 150 ml of 37° C. water into a 600-ml beaker containing 150 ml of 37° C. water. Tubes of prewarmed 50% PEG/ DMSO solution and serum-free RPMI 1640+Hepes solution are placed into one of the 37° C. water baths in the hood. The supernatant from the cell mixture is then aspirated and discarded.

Figure 7:
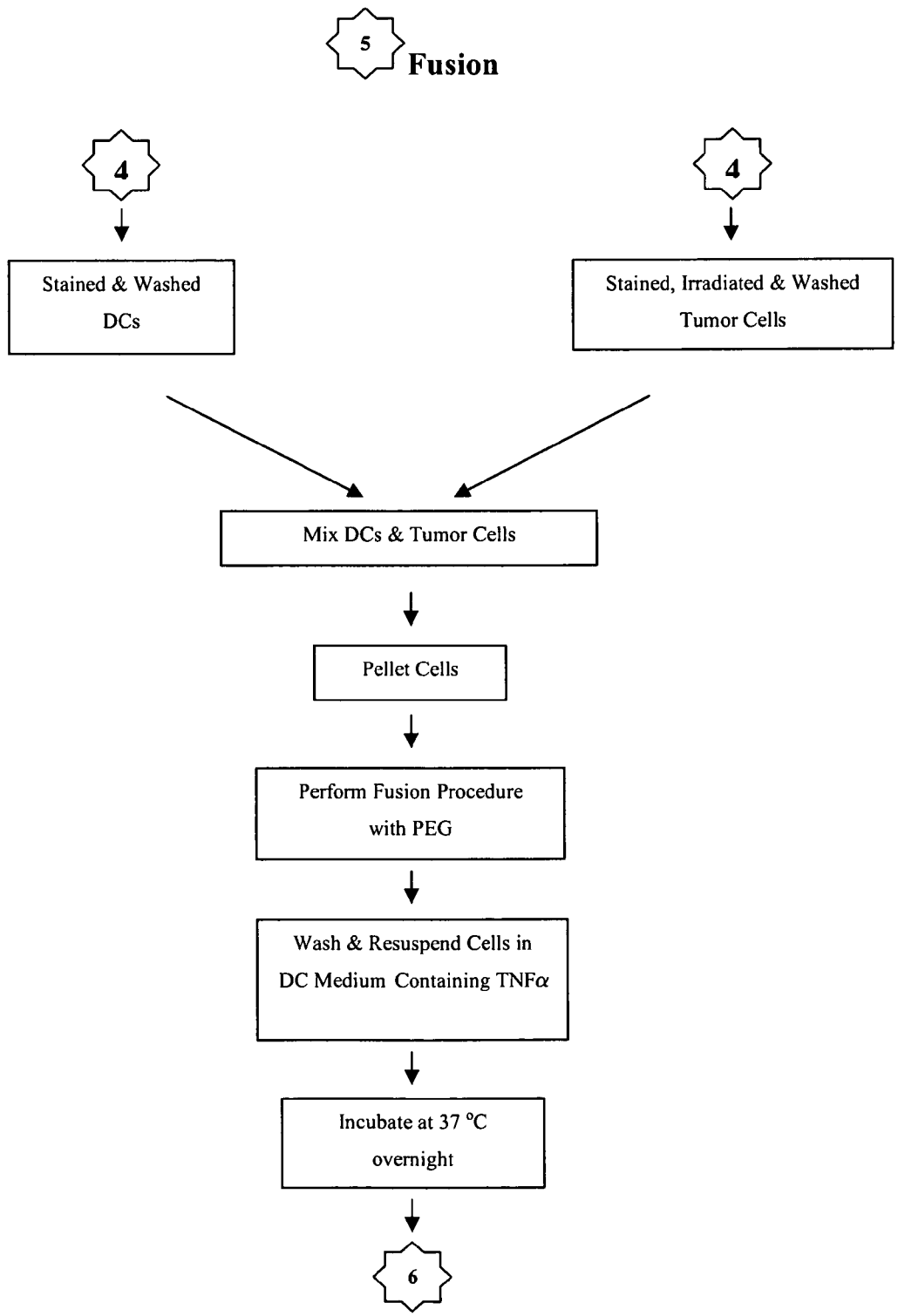
FIG. 7 is a flow diagram representing the cell fusion procedure.

Cell fusion is then performed at 37° C. by placing the tube containing the mixed-cell pellet in one of the double-beaker water baths in the laminar flow hood. One ml of prewarmed 50% PEG is added to the mixed-cell pellet drop-by-drop over one minute, stirring the cells with the pipette tip after each drop. The mixture is then stirred for an additional minute. Using a clean pipette, 2 ml of prewarmed RPMI 1640+ HEPES is added to the cell mixture drop-by-drop over 2 minutes, stirring after each drop. With a 10 ml pipette, 7 ml of prewarmed RPMI 1640+HEPES is added drop-by-drop over 2 to 3 minutes. This mixture is then centrifuged for five minutes at 500 g. While the cells are in the centrifuge, the double beakers are rewarmed to 37° C. and placed in the hood. Prewarmed, complete DC media containing 10% autologous serum is placed in the beaker water bath. The supernatant from the fusion mixture is then discarded and the tube is placed in the double-beaker water bath. With a pipette, 10 to 20 ml of prewarmed complete DC media containing 100 ng/ml TNFα are forcefully discharged onto the cell pellet and placed in a T75 flask. This cell mixture is incubated overnight in a humidifier at 37° C., 5% $CO_2$ incubator. FIG. 7 provides an overview of the cell fusion procedure.

C. Dendritoma Purification

Figure 8:
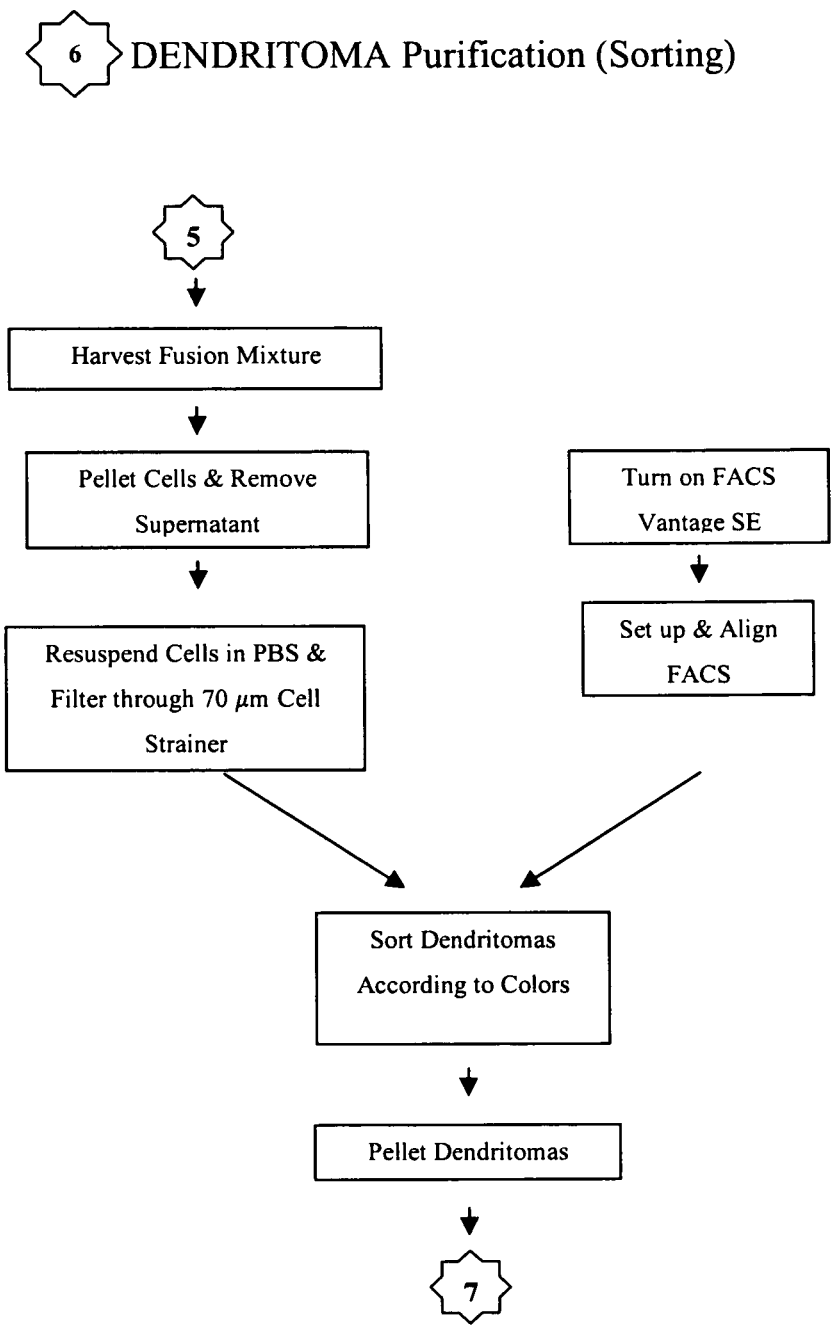
FIG. 8 is a flow diagram representing the steps for dendritoma purification.
Figure 9:
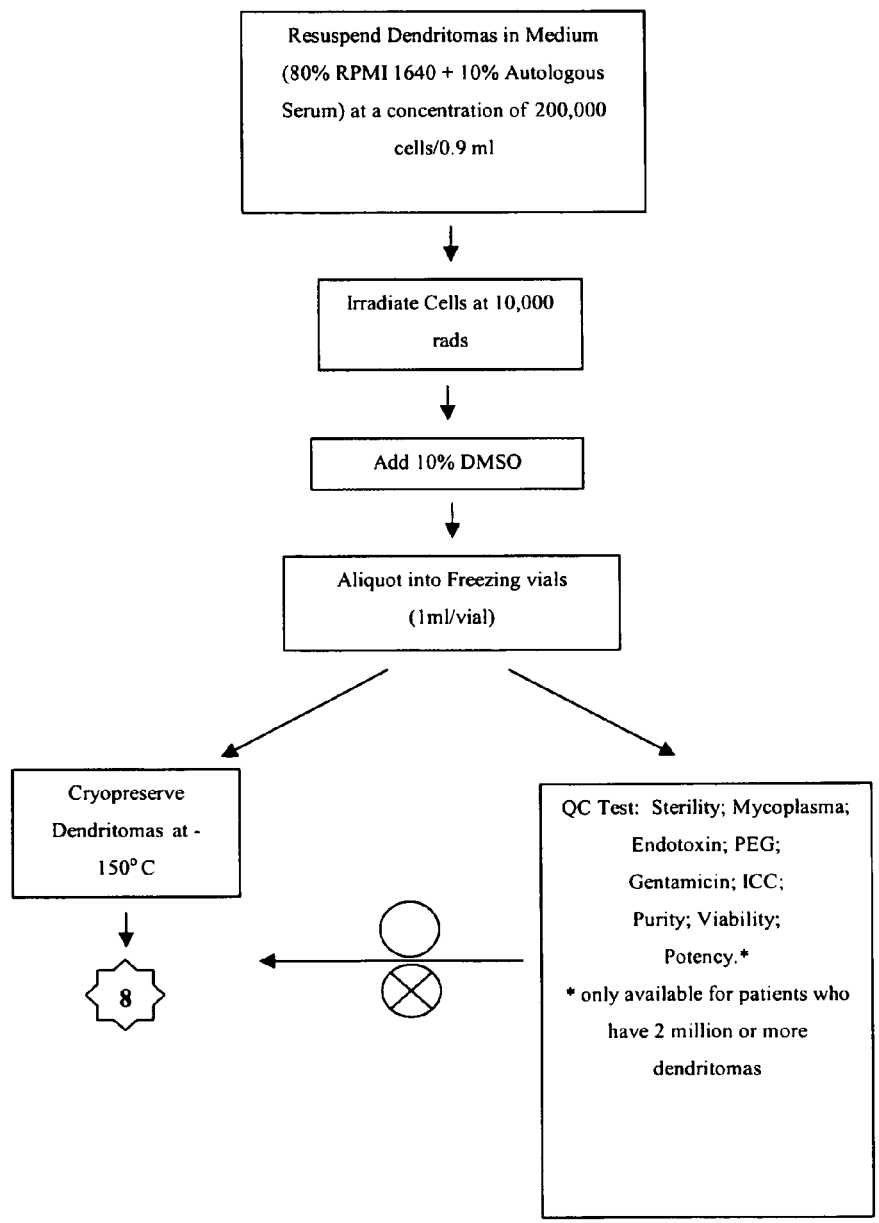
FIG. 9 is a flow diagram representing the procedure for dendritoma cryopreservation.

Following the fusion step, the fused cells are purified as shown in FIG. 8.

D. Final Product Formulation and Filling

Purified dendritomas are re-suspended in medium (80% RPMI-1640 and 10% autologous serum) at a concentration of 200,000 cells/0.9 ml medium and irradiated with 10,000 rads. Following irradiation, 10% DMSO is added and cells are aliquoted into 2 ml freezing vials (1 ml/vial). The last vial may contain less than 1 ml. The vials are cryopreserved at ≤150° C. in the liquid phase of a liquid nitrogen freezer designed to prevent contamination. All samples for release testing are obtained prior to cryopreservation. 2.0 ml cryovials are manufactured by Sarsted. These vials are transparent and in a conical shape. They are 10.8 mm in diameter and 46 mm in length, made of polypropylene and include an external thread format. The vials are sterile.

Example 4

Preparation of the Dendritoma Vaccine for Patient Administration

Figure 10:
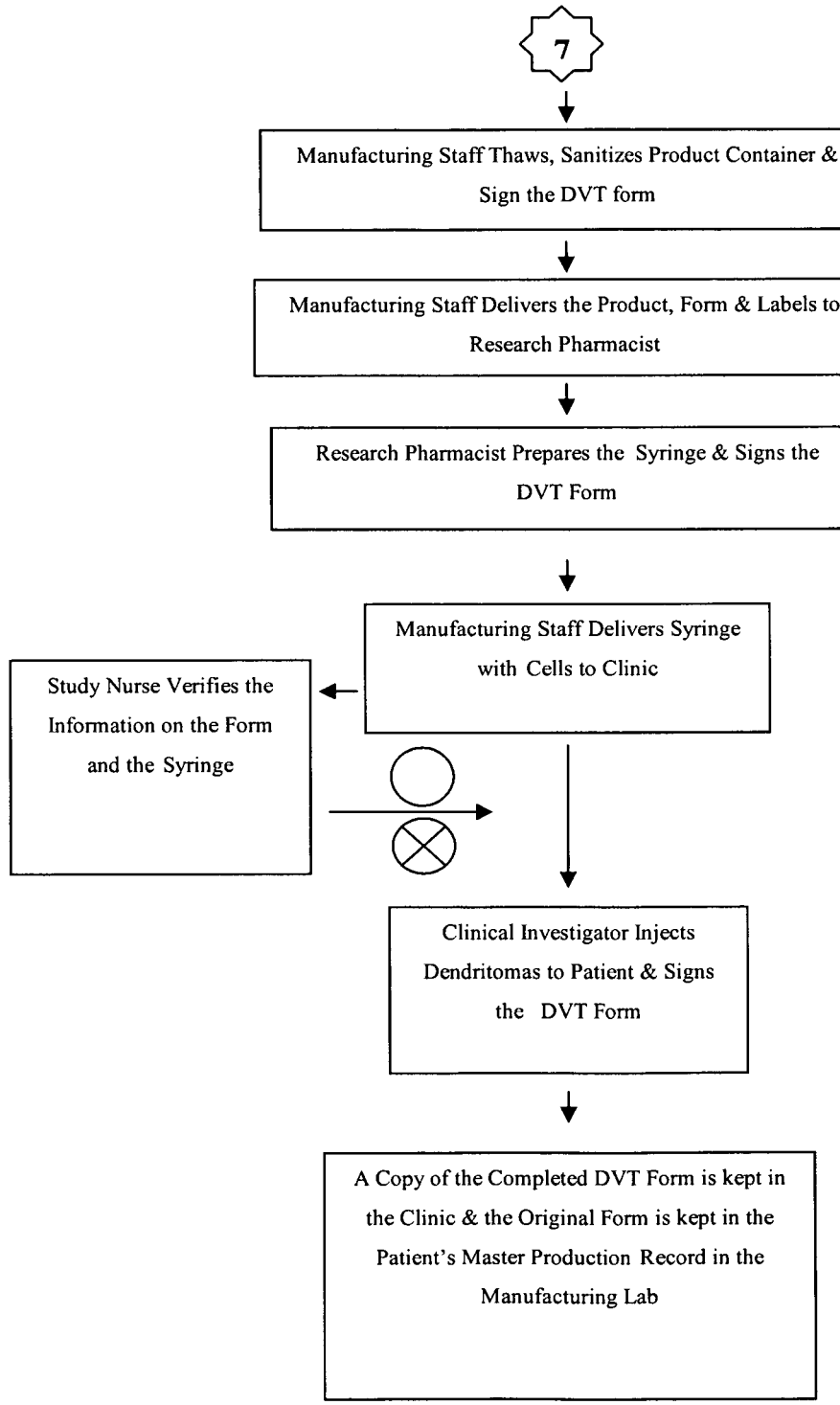
FIG. 10 is a flow diagram showing the process for pharmaceutical preparation and administration of the dendritoma vaccine to a patient.

The dendritoma vaccine vials are thawed at 37° C., formulated for patient administration and placed into labeled syringes. The content of the syringe is then administered subcutaneously to the patient. FIG. 10 provides an overview of the preparation and administration of the dendritoma vaccine.

Skin test tumor cells are thawed, formulated and placed into syringes like the dendritoma vaccine. The content of the syringe is then administered intradermally to the patient.

Example 5

Induction of Cancer Cell Specific Cytotoxic T Cell Response by the Dendritoma Vaccine This example demonstrates that the inventive hybrid cells induce a cancer cell-specific cytotoxic T cell response.

A. Cytotoxic T Cells

CD8+, cytotoxic T cells (CTLs) were prepared by the following method. Peripheral blood mononuclear cells (PBMC's) were isolated from whole blood by obtaining 40 ml of peripheral blood from the patient in preservative-free or sodium heparin tubes and 10 ml in ACD tubes. The blood was diluted 1:1 with 1×PBS. Eight ml of the diluted blood was layered over 4 ml of room temperature Ficoll-Paque Plus in 15 ml conical centrifuge tubes. The Ficoll gradients were centrifuged at 400 g at room temperature for 40 minutes. Using a Pasteur pipet, the PBMC layers were carefully removed from the Ficoll gradients and put into a sterile 15 ml centrifuge tube. Four volumes of 1×PBS were added to the tube and inverted several times to mix thoroughly. The PBMC's were centrifuged at 100 g at room temperature for 10 minutes. After removal of the supernatant, 10 ml of 1×PBS was added to the cells and inverted to mix. The PBMC's were pelleted by centrifugation at 100 g at room temperature for 10 minutes and resuspended in complete lymphocyte media (RPMI 1640, 10% FBS, 100 µg/ml gentamicin).

PBMC's were isolated from patients in preservative-free or sodium heparinized blood. They were subjected to the same panning technique as previously described except that anti-CD4 antibody was used to coat the plate. Prior to panning the PBMC's were enriched for T lymphocytes by passing them through a nylon wool column. This was done by packing 0.5 g of teased nylon wool into a 10 ml syringe which has a stopcock attached to the tip. The column was washed twice at 37° C. with RPMI 1640 with 10% FBS. The stopcock was closed and incubated at 37° C. for one hour. After draining the media from the column to the top of the wool, the PBMC's were added to the column (up to $2 \times 10^8$ in 2 ml of media). The stopcock was opened and the media was drained until the cell volume had entered the packed wool. After closing the stopcock, additional media was added to cover the top of the wool. The column was incubated for one hour at 37° C. The non-adherent T cells were collected by two media washes. After this T cell enrichment, the T lymphocytes were panned using the anti-CD4 coated plate. T cells that were not bound by the CD4 antibody were recovered and assumed to be CD8+ cells (cytotoxic T lymphocytes). This was confirmed by FACS analysis.

To have constant re-stimulators for tumor cell specific CTLs, the PBMC's isolated from the ACD blood were immortalized by Epstein-Barr virus (EBV) transformation. This was accomplished by resuspending the PBMC's at a concentration of $1 \times 10^6$ cells/ml in complete lymphocyte media. To this, 1 ml of EBV supernatant and 0.2 ml of phytohemagglutinin were added. The cell mixture was cultured in a T25 tissue culture flask at 37° C., 5% $CO_2$.

B. Stimulation of Cytotoxic T Cells

The instant dendritomas obtained from the FACS sort were mixed with the enriched, panned CD8+ T lymphocytes in a 1:10 ratio. The CD8+ cells to be used were pelleted by centrifugation at 1500 rpm for five minutes and resuspended in 1 ml of medium containing RPMI 1640, 10% FBS, 1000 U/ml IL-6, 5 ng/ml IL-12, and 10 U/ml IL-2. This was added to the instant dendritomas plated after the sort. This culture was incubated at 37° C., 5% $CO_2$ for one week. During that week the cells were refed with the same media.

After one week, the primed CD8+ T cells (CTLs) were restimulated with irradiated EBV-transformed lymphocytes that were pulsed with tumor lysate. Tumor cells, which had been previously cultured, were subjected to four freeze thaw cycles to lyse the cells. To obtain the lysate containing tumor antigens, the lysed cells were centrifuged at 600 g for ten minutes. The supernatant was collected and centrifuged at 13,000 g for one hour. The supernatant containing the lysate of tumor antigens was collected. To restimulate the CTLs a viable cell count was taken using trypan blue exclusion. Once the viable cell number was determined the same number of EBV transformed lymphocytes were pulsed with the tumor lysate by incubating the lysate with the lymphocytes at 37° C., 5% $CO_2$ for one hour. The pulsed lymphocytes were irradiated with 5,000 rads and then mixed with the CTLs in media containing RPMI 1640, 10% FBS, 10 U/ml IL-1α, 5 U/ml IL-2, 50 U/ml IL-4, 125 U/ml IL-6, and 30 U/ml IL-7. The culture was incubated at 37° C., 5% $CO_2$ and refed every two days. This re-stimulation was performed at 7 and 14 days after initial priming.

Each day the CTLs were refed, the supernatant that was removed was stored at −20° C. When feasible, an Interferon-gamma (IFN-γ) assay was performed using an OptEIA Human IFN-γ Kit (PharMingen). The protocol was performed exactly according to the manufacturer's directions. The assay was read using a Benchmark Microplate Reader (BioRad).

To determine if the instant dendritomas stimulated a tumor cell specific CTL response, a CTL assay was performed using the cultured tumor cells as target cells. Fifty thousand tumor cells were harvested and pelleted in a 15 ml conical centrifuge tube by centrifugation at 200 g for five minutes. The supernatant was discarded leaving 0.1 ml of medium on the pellet. The cells were gently resuspended in the remaining medium. The tumor cells were then labeled with $^{51}Cr$ by adding 0.1 ml of 1 mCi/ml $^{51}Cr$ solution and 10 µl FBS and mixing gently. This mixture was incubated by loosening the cap of the tube and placing at 37° C., 5% $CO_2$ for one hour. After the incubation, the labeled tumor cells were washed twice with 14 ml of RPMI 1640 and resuspended at a concentration of $5\times10^4$ cells/ml in complete lymphocyte media.

The CTL effector cells were plated in 4 wells of a round bottom 96 well tissue culture plate at concentrations that equaled 100:1, 30:1, 10:1, and 3:1 effector to target cell ratios. Five thousand labeled target cells were added to the wells containing the effector cells as well as two additional wells for natural and maximum release controls. The cells were mixed and centrifuged at 200 g for 30 seconds. The plate was then incubated at 37° C., 5% $CO_2$ for four hours. Thirty minutes prior to the end of the incubation, 0.1 ml of Triton X-100 was added to the maximum release control well. At the end of the incubation, the cells were centrifuged in the plate at 200 g for five minutes. 0.1 ml of each supernatant was added to liquid scintillation counter vials containing 5 ml of scintillation cocktail. The amount of $^{51}Cr$ release was measured using a LS6500 Multi-purpose Scintillation Counter (Beckman).

The CTL assay results showed that as the ratio of hybrid cell-primed CTLs to tumor cells increased, the release of the isotope increased, indicating a positive correlation between the number of CTLs and tumor killing. Greater than 50% killing was observed at a 100:1 effector:target ratio. On the other hand, there was no such correlation with control T cells that were not primed with the inventive hybrid cells. Even at a ratio of 100:1, the control T cells did not lyse more tumor cells than at lower ratios. These results demonstrated that the CTLs generated using our hybrid antigen presenting cells are fully functional and tumor cell specific. The results are depicted in FIG. 1.

Example 6

Dendritoma Characterization

This example provides further characterization of the reactant cells and the dendritomas described in the Examples above.

Fluorescent microscopic analysis showed that 100% of the stained cells were successfully labeled. To test whether the dye can interstain between the two different type of cells, green DCs and red tumor cells were mixed together and incubated overnight. Fluorescent microscopic examination showed there was no interstaining. Immediate examination of the fusion product demonstrated that the green DCs and the red tumor cells were fused together and after an overnight recovery, the fused cells showed both colors. The double colored cells (approximately 10% of the total cells), instant dendritomas, were then purified by FACS sorting. More than 95% of the sorted cells were double colored fused cells.

Figure 2A:
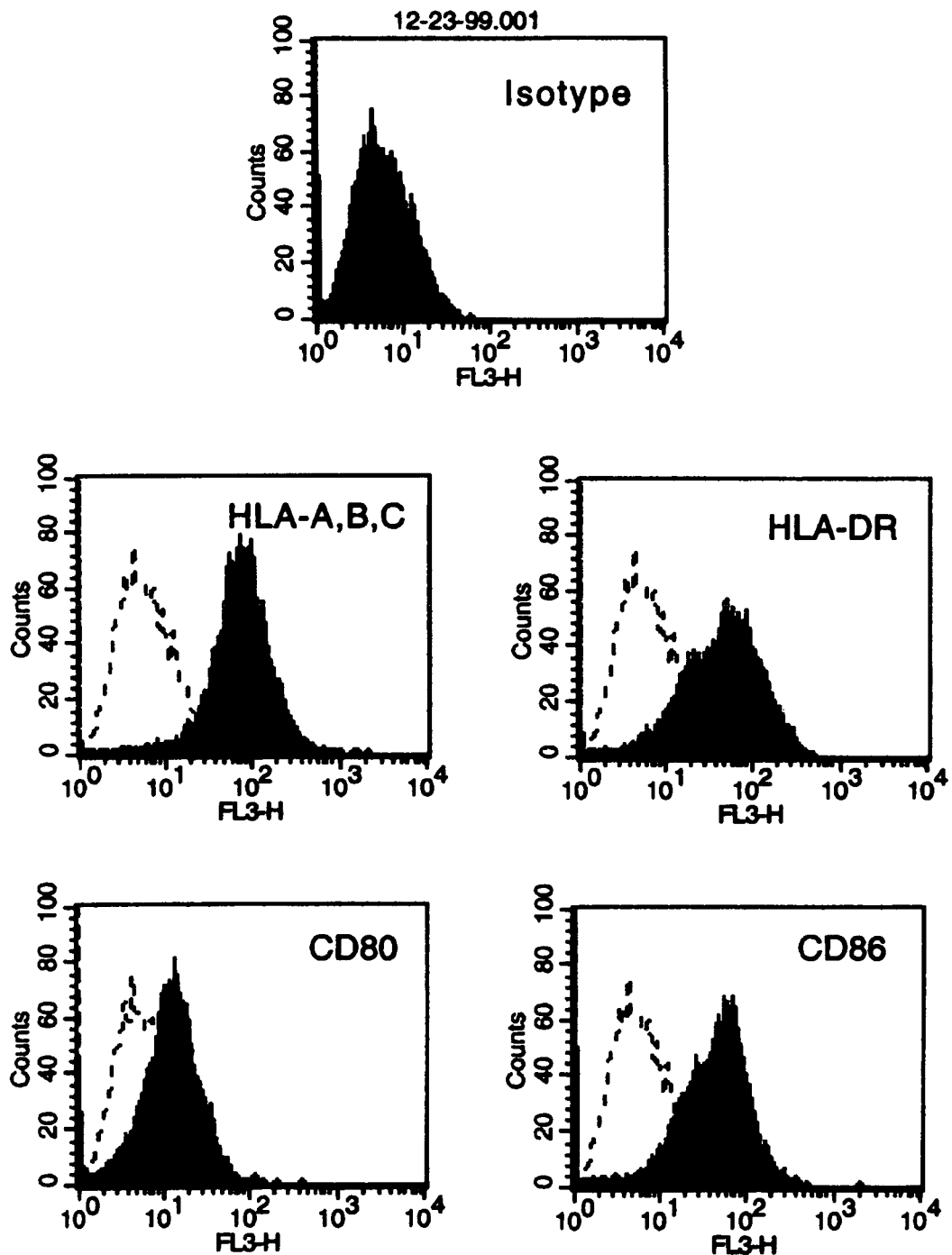
FIG. 2A shows FACS-detection of antigen-presentation markers on control dendritic cells. A normal distribution is shown.
Figure 2B:
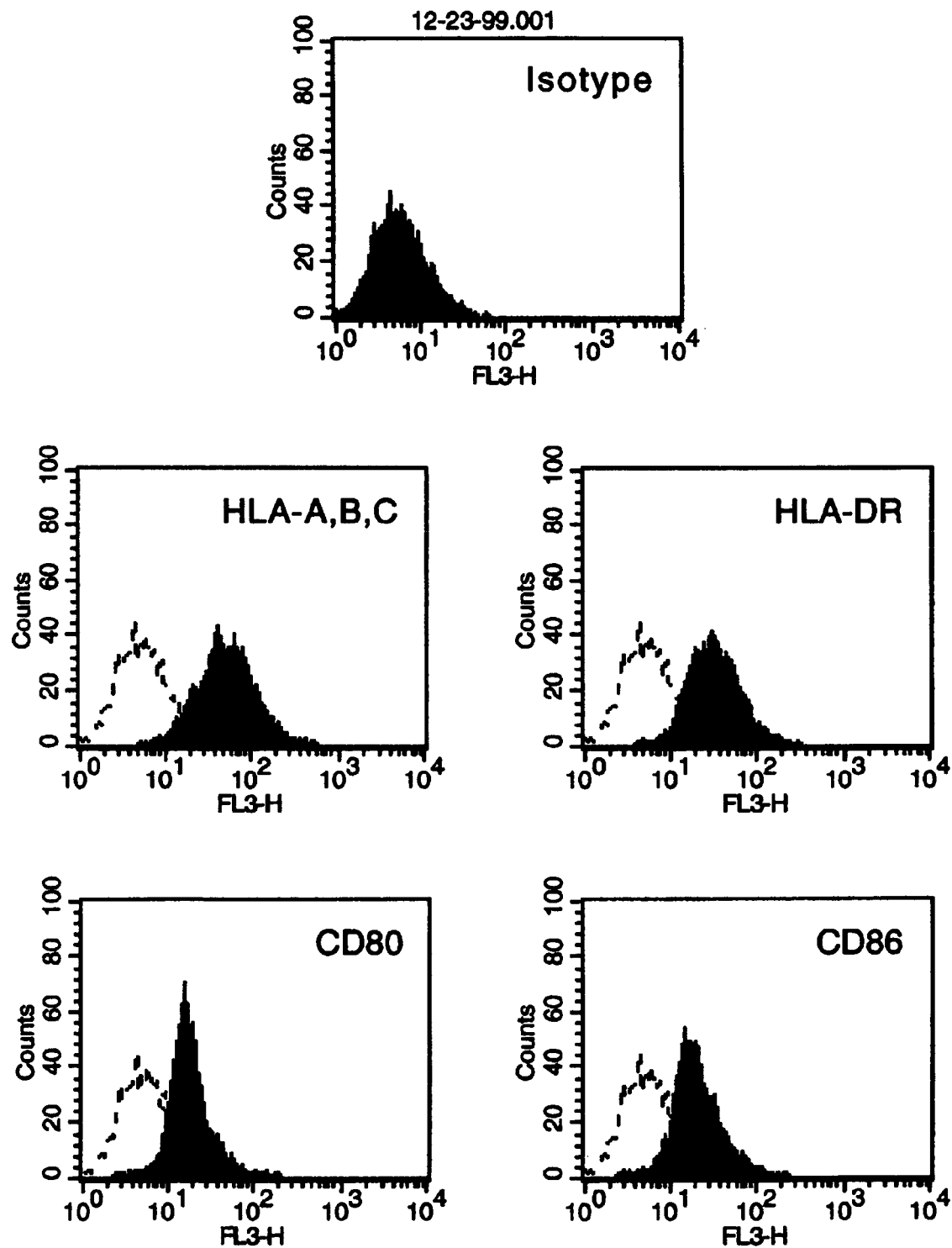
FIG. 2B shows FACS-detection of antigen-presentation markers on dendritic/tumor cell hybrids. A normal distribution is shown, as compared to the control dendritic cells, meaning that the hybrid cells retain all of the markers necessary for antigen presentation.

Instant dendritomas express all the molecules necessary for antigen presentation. FACS analysis showed that instant dendritomas express the molecules required for antigen presentation, such as MHC class I and II and co-stimulating molecules CD80 (B7.1) and CD86 (B7.2). The data are depicted in FIG. 2. "Isotype" is the negative control; HLA-A,B,C is MHC class I and HLA-DR is MHC class II. Under a microscope, moreover, instant dendritomas also have those dark granules that melanoma tumor cells have.

For FIG. 2, human DCs from peripheral blood were stained with the green dye and tumor cells were stained with the red dye, respectively, and fused, using the above protocol. After overnight incubation, the cells were equally divided into 4 groups. They were then stained with Cy-Chrome conjugated antibodies by incubating the cells with the antibodies (1 million cells/microgram antibody, Becton/Dickinson) on ice for 30 min. The different groups were as follows: anti-human HLA-A,B,C [group I]; anti-human HLA-DR [group II]; anti-human CD80 [group III]; and anti-human CD86 [group IV]. The un-bound antibodies were removed by two washes and the cell pellet was re-suspended in 0.5 ml of staining buffer (PBS containing 0.1% BSA and 0.1% sodium azide). Three-color analysis was performed by FACS, using CellQuest software. Control human DCs were also stained with the same antibodies in the same way.

Example 7

Clinical Protocol

This example provides an exemplary clinical protocol for treating human cancer patients with the inventive hybrid cell preparations in conjunction with BCG therapy. This regimen is useful, for example, to treat neuroblastoma patients with a dendritoma vaccine in combination with BCG therapy, prepared according to the inventive methodologies.

A. Blood Draws for Dendritic Cells and Serum Preparation

For culture of the patient's dendritic cells and cryopreservation of the patient's tumor cells and dendritomas, the patient's own autologous serum is used, however, commercially available serum free dendritic cell media may also be used. Serum is isolated using standard procedures from 100 mL of peripheral blood collected without anti-coagulants. In order to generate the dendritoma vaccine, dendritic cells are harvested from the patient. Three hundred milliliters of sodium heparinized peripheral blood is collected from the patient.

Additional blood draws for dendritic cells and/or serum are required for the generation of the vaccine. Two or 3 blood draws may be necessary to obtain an adequate number of dendritic cells. Additional autologous serum may also need to be isolated. However, additional blood draws for dendritic cells and serum are determined by the patient's hemoglobin level assessed after each blood draw. Blood is drawn from the patient if the hemoglobin level is greater than or equal to 8.5 mg/dL. If the hemoglobin level is below 8.5 mg/dL, the patient will receive packed red blood cells prior to having the next blood draw to increase the hemoglobin level.

B. Dendritic Cell Generation

Mature dendritic cells are generated from the patient's peripheral blood monocytes (PBMCs). In one embodiment, the dendritic cells are generated by leukapheresis, which is the selective separation and removal of leukocytes from withdrawn blood, the remainder of the blood is then retransfused into the donor. In another embodiment, 300 mls of peripheral blood are obtained from the patient in preservative free or sodium heparin tubes. Briefly, the blood is diluted 1:1 with 1×PBS. Then, 8 mls of the diluted blood are layered over 4 mls of room temperature Ficoll-Paque Plus in a 15 ml centrifuge tube, and centrifuged at 40 g for 40 minutes. The PBMC layer is removed from the Ficoll gradient, and placed into a clean 250 ml centrifuge tube. 4 volumes of 1×PBS are added and the tube is inverted to mix. The PBMC's are then centrifuged at 100 g at room temperature for 10 minutes. 10 ml of 1×PBS are added, and the cells are mixed by inverting the tube. The PBMC's are again centrifuged at 100 g at room temperature for 10 minutes. The PBMC's are resuspended in 5 ml complete DC medium (RPMI 1640+10% human serum+ 800 U/ml GM-CSF+1000 U/ml IL-4). Then the dendritic cells/precursors are optionally panned using anti-CD14 coated plates. $2\times10^8$ PBMC's are placed onto the anti-CD14 coated plate and swirled. They are left to incubate at room temperature for 30 minutes. The non-adherent cells are then removed. 10 ml of 1×PBS are added, the plate is swirled, and the PBS is removed. This PBS washing is repeated for a total of four times, pipetting at the same place each time. Afterwards, 10 ml of complete DC media is added to the plate. They are then incubated at 37° C., 5% $CO_2$ for 5-10 days to generate dendritic cells.

C. Tumor Cells

A tumor section is obtained at the time of biopsy or excisional resection. The tumor cells are cultured using the following technique. After separating fat and necrotic tissue away from the tumor tissue (1-5 grams), the tumor is cut into small chunks and put into a T 75 flask. This solution will rock for 1 hour at 37° C., and then 15 ml of complete media (DMEM+10% human serum+gentamicin) are added. The chunks are then removed and put into a clean T75 flask. This flask is left at 37° C. in 5% $CO_2$ overnight. Then the cell suspension/typsin/complete media is centrifuged at 1000 g for 5 minutes. These cells are resuspended in 15 ml of complete media and cultured in a T75 flask at 37° C. in 5% $CO_2$ for 24 hours. After overnight incubation in the absence of media, 20 ml of complete media are added to the flask with chunks, and this solution is left for two days at 37° C. in 5% $CO_2$. The chunks are removed, and the adherent cells are cultured. The tumor cells used for dendritic fusion result from both cultures.

D. Hybrid Formation

The next step comprises the fusion of tumor cells and dendritic cells received from the patient. Hybrid formation by cell fusion became routine after the introduction of the use of polyethylene glycol as a fusing agent. The procedure outlined below is a variation of the one reported by Prado et al., 1989 *FEBS Lett.,* 259: 149-52, for the PEG-mediated fusion of somatic cells in monolayers.

First, the tumor cells are exposed to a single dose of 5000 rads, sufficient to kill all of the cells. Then, the dendritic cells are stained green using the PKH2-GL fluorescent dye (Sigma), and the tumor cells are stained red using the PKH26 fluorescent dye (Sigma). The staining procedure is performed at 25° C., using a slight modification of the Sigma procedure. The cells to be stained are washed with serum-free media. The cell suspension is centrifuged at 400 g for five minutes to obtain a loose pellet, and the supernatant fraction is removed. The pellet is resuspended by tapping the centrifuge tube, and 1 ml of diluent (20% DMSO in serum-free RPMI) is added to resuspend the cells. Immediately prior to staining, $4 \times 10^{-6}$ molar dyes (2×) were prepared with diluent in polypropylene tubes. The cells in the diluent are rapidly added into 1 ml of 2× dye, and the mixture is immediately mixed by gentle pipetting. The mixture is then incubated at 25° C. for five minutes. The staining process is stopped by adding an equal volume of 10% human serum, which may be the patient's own serum, and incubating for one minute. The stained cells are diluted with equal volume of complete culture medium. Stained cells are removed from the staining solution by centrifuging at 400 g for 10 minutes.

The green dendritic cells are mixed with the red tumor cells at a 1:1 ratio in a 50-ml conical centrifuge tube. The tube is filled with complete serum-free DMEM. The cell mixture is centrifuged for 5 minutes at 500 g. While the cells are being centrifuged, three 37° C. double-beaker water baths are prepared in the laminar flow hood by placing a 400-ml beaker containing 100 ml of 37° C. water into a 600-ml beaker containing 75 to 100 ml of 37° C. water. Tubes of prewarmed 50% PEG solution and complete serum-free DMEM are placed into two of the 37° C. water baths in the hood. Then, the supernatant from the cell mixture is aspirated and discarded. The cell fusion is performed at 37° C. by placing the tube containing the mixed-cell pellet in on of the double-beaker water baths in the laminar flow hood. Then, 1 ml of prewarmed 50% PEG is added to the mixed-cell pellet drop-by-drop over one minute, stirring the cells with the pipette tip after each drop. The mixture is then stirred for an additional minute.

Using a clean pipette, 1 ml of pre-warmed RPMI+HEPES is added to the cell mixture drop-by-drop over one minute, stirring after each drop. This step is repeated once with an additional 1 ml of prewarmed RPMI+HEPES solution. With a 10-ml pipette, 7 ml of prewarmed RPMI+HEPES is added drop-by-drop over 2 to 3 minutes. This mixture is then centrifuged for five minutes at 500 g. While the cells are in the centrifuge, the water baths are rewarmed to 37° C. and placed in the hood. Prewarmed complete DC media is placed in the beaker water bath. Then the supernatant from the mixture is discarded; the tube is placed in the beaker water bath. With a pipette, 10 ml of prewarmed complete DC media are forcefully discharged onto the cell pellet and placed in a T75 flask. This is incubated overnight in a humidified 37° C., 5% CO2 incubator.

The next day, the cells are analyzed on a FACS Caliber fluorescence activated cell sorter using the CELLQuest software (Becton/Dickenson), which will sort the fusion cells with both the green and red dye. These fusion cells, dendritomas, are then resuspended in 1 ml of NS (Normal Saline) and injected into the patient.

E. The Dendritoma Vaccine

The vaccine consists of at least 100,000 (or more) irradiated tumor cells fused to dendritic cells i.e. dendritomas. A minimum dose of 100,000 dendritomas is administered during each vaccination. These dendritomas are resuspended in 1 ml of normal saline (NS) and injected subcutaneously into an area of lymph nodes in the axilla or inguinal area of the patient. The injection site is rotated to avoid injection in the same lymph node bed on two consecutive administrations. After the initial vaccination, the patient is revaccinated every 6 weeks. The patient may receive a maximum of 6 vaccinations, depending on the total number of dendritomas obtained.

The BCG preparation is administered subcutaneously within 10 minutes of the administration after each dose of the dendritoma vaccine. The dosage of BCG (*Mycobacterium bovis* bacillus Calmette-Guerin) to be administered after the initial vaccination with the dendritoma vaccine is based upon the patient's reaction to the TB skin test administered prior to BCG administration. Depending on the patient's reaction to the TB skin test, the BCG composition consists of at least 20,000 units, preferably at least 250,000 units, and more preferably at least 1,000,000 units of BCG (see Table 1 above). The BCG therapy is administered subcutaneously within 10 minutes of the administration after each dose of the dendritoma vaccine.

Following administration of the second dendritoma vaccine, within 10 minutes of vaccination, the patient is administered a second BCG preparation. Preferably, the BCG preparation is administered at the same dosage as the first BCG preparation, unless the initial injection produced ulceration at the injection site. If ulceration occurs at the injection site after the initial administration, half the dose (50% of the BCG dose) of the initial vaccination is used.

Subsequent administration of BCG preparation is based on the patient's reaction to previous BCG administration. Preferably, the BCG preparation is administered at the same dosage as the first BCG preparation, unless the initial injection produced ulceration at the injection site. If ulceration occurs at the injection site after the dosage of BCG is reduced by 50%, then BCG is not administered and the dendritoma vaccine is administered alone on all subsequent injections.

Interleukin 2 (e.g., Aldesleukin) also may optionally be given in a low-dose regimen. When used, IL-2 is administered by subcutaneous injection in a dosage of 18 million units daily for 5 days beginning on the day of vaccination.

Example 8

Clinical Trials

Patient 1 with metastatic stage IV neuroblastoma (staged according the International Neuroblastoma Staging System INSS) exhibited paraplegia secondary to tumor around the spinal cord. The primary tumor was suprarenal with erosion through the spinal column. The cancer was spread to distant sites, including the patient's bone marrow, liver and lumbar vertebrae. The tumor was not n-myc amplified. The patient had 7 cycles of chemotherapy and after completing therapy underwent surgery to remove the bulk tumor on the right suprarenal area. Bone marrow aspirate and biopsy showed persistent neuroblastoma. CT scans of chest, abdomen and pelvis showed persistent disease in the liver and lumbar vertebrae. The patient was not a candidate for bone marrow transplant because of persistent disease in the bone marrow.

Patient 1's tumor cells, after irradiation, were fused with their dendritic cells to produce a non-proliferative hybrid cell, also known as a dendritoma. The dendritomas were obtained and counted before administration and the patient was vaccinated with the dendritoma vaccine approximately every six weeks following the initial vaccination according to the following scheme:

| Administration Time Line (Post initial treatment) | Dendritoma Dose | CFU of BCG administered |
|---|---|---|
| Initial Treatment - 0 weeks | 275,000 cells | 1,000,000 |
| Second Treatment - 6 weeks | 275,000 cells | 1,000,000 |
| Third Treatment - 12 weeks | 210,000 cells | 1,000,000 |
| Fourth Treatment - 18 weeks | 200,000 cells | 500,000 |
| Fifth Treatment - 24 weeks | 200,000 cells | 0 |

The dendritoma vaccine was injected subcutaneously into an area of lymph nodes in the axilla or inguinal area of the patient.

BCG was administered to patient 1 subcutaneously into an area of lymph nodes in the axilla or inguinal area of the patient within 10 minutes of the first four dendritoma doses. The BCG used in this study is commercially available and is manufactured by Organon Teknika Corporation (Durham, N.C.). All BCG injections where administered within 10 minutes of the dendritoma vaccine.

The injection sites for the dendritoma vaccine and the BCG preparation can be rotated to avoid injection in the same lymph node bed on two consecutive administrations, by alternating anterior and posterior injections with lateral and medial injections.

The dendritoma vaccine and the BCG preparations were not mixed and the BCG dosage was determined based upon the patient's reaction to the TB skin test administered prior to the study entry. Administration of the BCG dosage followed the following scheme:

| TB Skin Test Result | Dermatologic Reaction | BCG Dose |
|---|---|---|
| Negative | None | 1,000,000 units |
| Positive | <10 mm in duration | 250,000 units |
| Positive | ≥10 mm in duration, erythema | 20,000 units |

BCG is measured in colony forming unit (CFU). For example, 20,000 BCG units on a culture plate will produce 20,000 bacterial colonies.

In this case, the TB skin test results for Patient 1 were negative, and the initial BCG dose administered with the dendritoma vaccine to Patient 1 was therefore 1,000,000 CFU.

For the second vaccination, the same BCG dose as the initial vaccination is used, unless the initial injection produces ulceration at the injection site. If ulceration occurs, half the dose (50% of the BCG dose) of the initial vaccination is used. In this case, Patient 1 was administered a BCG dose of 1,000,000 CFU for the second vaccination.

For subsequent vaccinations, the same BCG dose as the initial vaccination is used, unless the initial injection produces ulceration at the injection site. If ulceration occurs after the dosage of BCG is decreased by 50%, then BCG is not administered again and the dendritoma vaccine is given without the BCG on all subsequent injections. If, however, no ulceration occurs after the dosage of BCG is decreased by 50%, then BCG is administered again using the same decreased dosage. In this case, ulceration occurred in Patient 1 after the dosage of BCG was decreased by 50%, so the fifth vaccine was administered without concomitant BCG.

Patient 1 showed great improvement at the end of the treatment with the dendritoma vaccine and the BCG preparation according to the invention. As a result of the treatment, the progression of the neuroblastoma in the patient has considerably slowed and the patient's life expectancy has dramatically increased.

Table 4 and Table 5 below summarize the studies performed prior, during and after the initial vaccination (Table 2), and before and after the second vaccination (Table 3).

TABLE 4

The schedule of time and events prior to study entry, during, and following the initial vaccination

| Procedure | Prestudy | Day 0 | Day 1[#] | Weeks 2-5[##] | Week 6[##] |
|---|---|---|---|---|---|
| Informed consent | X | — | — | — | — |
| 100 cc blood draw for serum | X | — | — | — | — |
| 300 cc blood draw with Heparin | X | — | — | — | — |
| HIV 1, 2; Hepatitis A, B and C | X | — | — | — | — |

TABLE 4-continued

The schedule of time and events prior to study entry, during, and following the initial vaccination

| Procedure | Prestudy | Day 0 | Day 1[#] | Weeks 2-5[##] | Week 6[##] |
|---|---|---|---|---|---|
| Complete Blood Count | X | — | X | X | X |
| Complete Metabolic Profile | X | — | X | X | X |
| Physical examination | X | X | — | — | X |
| Vital signs and weight | X | X | X | X | X |
| SAE monitoring[$] | | <---------------------------------------> | | | |
| PPD skin test | X | — | — | — | — |
| Serum pregnancy test | X | | | | |
| Vaccine administration | — | X | — | — | — |
| BCG administration | — | X | — | — | — |

[#]Within 2 days
[##]Within +/− 7 days
[$]SAEs will be monitored from the first vaccination until six weeks after the last vaccination.
*Every 8 to 10 weeks

TABLE 5

The schedule of time and events prior to and after revaccination

| Procedure | Every 6 weeks prior to revaccination*[####] | Day 0 vaccine | Day 1[#] | Weeks 2-5[##] | Week 6[##] |
|---|---|---|---|---|---|
| CBC | X | — | X | X | X |
| CMP | X | — | X | X | X |
| Vital signs/weight | X | X | X | X | X |
| SAE monitoring[$] | | <---------------------------------------> | | | |
| Physical examination | X | X | — | — | X |
| HIV 1, 2; Hepatitis A, B and C[††] | X | | | | |
| CT scans[†] | — | — | — | X | — |
| Bone marrow aspirated biopsy[†] | — | — | — | X | — |
| Serum pregnancy test | X | | | | |
| Vaccine administration | — | X | — | — | — |
| BCG administration | — | X | — | — | — |

*Also the 6-week follow-up
Within 2 days
Within +/− 7 days
[$]SAEs will be monitored from the first vaccination until six weeks after the last vaccination.
[†]Every 8 to 10 weeks
[††]Performed annually It will be apparent to those skilled in the art that various modifications and variations can be made in the methods and compositions of the present invention without departing from the spirit or scope of the invention. Thus, it is intended that the present invention cover the modification and variations of the invention provided they come within the scope of the appended claims and their equivalents.

The invention claimed is:

1. A composition comprising a hybrid cell preparation, wherein the hybrid cell preparation is prepared by a method comprising:
    (a) staining a neoplastic cell population freshly isolated from a patient without culturing with a first marker,
    (b) staining a dendritic cell population with a second marker, wherein the first marker is different from the second marker,
    (c) contacting the neoplastic cell population and the dendritic cell population with one another under conditions that promote cell fusion,
    (d) obtaining a resultant hybrid cell population stained with both the first and second markers, and
    (e) purifying the resultant hybrid cell population;
wherein the method does not involve antibiotic or metabolic selection, the purifying is accomplished in less than about 24 to 48 hours after said contacting.

2. The composition of claim 1, wherein the first marker is a fluorescent dye, the second marker is a fluorescent dye, and the resultant hybrid cell population is purified by fluorescence activated cell sorting.

3. The composition of claim 1, wherein less than 10% of the resultant hybrid cell population is reactant cells.

4. The composition of claim 1, wherein less than 5% of the resultant hybrid cell population is reactant cells.

5. The composition of claim 1, further comprising a pharmaceutically acceptable vehicle.

6. The composition of claim 2, wherein the first and second fluorescent dyes are endotoxin-free, pyrogen-free or both.

7. The composition of claim 1, wherein the neoplastic cell is a tumor cell.

8. The composition of claim 7, wherein the tumor cell is a primary tumor cell.

9. A method of treating cancer, comprising:
    (i) providing a hybrid cell preparation prepared by a method comprising:
        (a) staining a neoplastic cell population freshly isolated from a patient without culturing with a first marker, (b) staining a dendritic cell population with a second marker, wherein the first marker is different from the second marker, (c) contacting said neoplastic cell population and the dendritic cell population with one another under conditions that promote cell fusion, (d) obtaining a resultant hybrid cell population stained with both the first and second markers, and (d) purifying the resultant hybrid cell population;

wherein the method does not involve antibiotic or metabolic selection, said purifying is accomplished in less than about 24 to 48 hours after the contacting;

(ii) resuspending the resultant hybrid cell preparation in a pharmaceutically acceptable vehicle, and (iii) administering the hybrid cell preparation to a cancer patient.

10. The method of claim 9, wherein the first marker is a fluorescent dye, the second marker is a fluorescent dye, and the resultant hybrid cell population is purified by fluorescence activated cell sorting.

11. A cancer vaccine comprising a hybrid cell preparation and a pharmaceutically acceptable vehicle, wherein the hybrid cell preparation is prepared by a method comprising:

(a) staining a neoplastic cell population freshly isolated from a patient without culturing with a first marker, (b) staining a dendritic cell population with a second marker, wherein the first marker is different from the second marker, (c) contacting the neoplastic cell population and the dendritic cell population with one another under conditions that promote cell fusion, (d) obtaining a resultant hybrid cell population stained with both the first and second markers, (e) purifying the resultant hybrid cell population, and (f) resuspending the resultant hybrid cell population in a pharmaceutically acceptable vehicle;

wherein the method does not involve antibiotic or metabolic selection, the purifying is accomplished in less than about 24 to 48 hours after the contacting.

12. The cancer vaccine of claim 11, wherein the first marker is a fluorescent dye, the second marker is a fluorescent dye, and the resultant hybrid cell population is purified by fluorescence activated cell sorting.

13. The cancer vaccine of claim 11, wherein the pharmaceutically acceptable vehicle is saline.

14. A tumor vaccine comprising a hybrid cell preparation and a pharmaceutically acceptable vehicle, wherein the hybrid cell preparation is prepared by a method comprising:

(a) staining a neoplastic cell population freshly isolated from a patient without culturing with a first marker, (b) staining a dendritic cell population with a second marker, wherein the first marker is different from the second marker, (c) contacting the neoplastic cell population and the dendritic cell population with one another under conditions that promote cell fusion, (d) obtaining a resultant hybrid cell population stained with both the first and second markers, (e) purifying the resultant hybrid cell population, and (f) resuspending the resultant hybrid cell population in a pharmaceutically acceptable vehicle;

wherein the method does not involve antibiotic or metabolic selection, the purifying is accomplished in less than about 24 to 48 hours after the contacting.

15. The tumor vaccine of claim 14, wherein the first marker is a fluorescent dye, the second marker is a fluorescent dye, and the resultant hybrid cell population is purified by fluorescence activated cell sorting.

16. The tumor vaccine of claim 14, wherein the pharmaceutically acceptable vehicle is saline.

17. A kit comprising (i) at least two dyes that are essentially endotoxin-free or pyrogen-free or both; and (ii) instructions for preparing hybrid cells from reactant cells by a method comprising:

(a) staining a neoplastic cell population freshly isolated from a patient without culturing with a first dye from the at least two dyes, (b) staining a dendritic cell population with a second dye from the at least two dyes, wherein said first dye is different from said second dye, (c) contacting said neoplastic cell population and said dendritic cell population with one another under conditions that promote cell fusion, (d) obtaining a resultant hybrid cell population stained with both the first and second dyes, and (e) purifying the resultant hybrid cell population;

wherein said method does not involve antibiotic or metabolic selection, said purifying is accomplished in less than about 24 to 48 hours after said contacting.

* * * * *

UNITED STATES PATENT AND TRADEMARK OFFICE
CERTIFICATE OF CORRECTION

| | |
|---|---|
| PATENT NO. | : 8,785,186 B2 |
| APPLICATION NO. | : 12/461760 |
| DATED | : July 22, 2014 |
| INVENTOR(S) | : Wagner et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

Signed and Sealed this
Third Day of May, 2016

Michelle K. Lee
*Director of the United States Patent and Trademark Office*